United States Patent
Runyon et al.

(10) Patent No.: US 11,142,546 B2
(45) Date of Patent: Oct. 12, 2021

(54) NEUROPEPTIDE S RECEPTOR (NPSR) AGONISTS

(71) Applicant: Research Triangle Institute, Research Triangle Park, NC (US)

(72) Inventors: Scott Runyon, Hillsborough, NC (US); Carla Hassler, Durham, NC (US); Craig Shiner, Durham, NC (US); Sanju Narayanan, Durham, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 16/090,726

(22) PCT Filed: Mar. 23, 2017

(86) PCT No.: PCT/US2017/023762
§ 371 (c)(1),
(2) Date: Oct. 2, 2018

(87) PCT Pub. No.: WO2017/176461
PCT Pub. Date: Oct. 12, 2017

(65) Prior Publication Data
US 2019/0092809 A1  Mar. 28, 2019

Related U.S. Application Data

(60) Provisional application No. 62/318,042, filed on Apr. 4, 2016.

(51) Int. Cl.
| | |
|---|---|
| C07K 5/02 | (2006.01) |
| C07K 5/065 | (2006.01) |
| A61K 31/4015 | (2006.01) |
| A61K 31/55 | (2006.01) |
| C07D 207/416 | (2006.01) |
| A61K 31/495 | (2006.01) |
| A61P 25/20 | (2006.01) |
| C07C 237/24 | (2006.01) |
| A61P 25/30 | (2006.01) |
| C07D 211/60 | (2006.01) |
| C07D 223/20 | (2006.01) |
| C07K 11/00 | (2006.01) |
| A61K 38/00 | (2006.01) |

(52) U.S. Cl.
CPC ........ *C07K 5/0202* (2013.01); *A61K 31/4015* (2013.01); *A61K 31/495* (2013.01); *A61K 31/55* (2013.01); *A61P 25/20* (2018.01); *A61P 25/30* (2018.01); *C07C 237/24* (2013.01); *C07D 207/416* (2013.01); *C07D 211/60* (2013.01); *C07D 223/20* (2013.01); *C07K 5/06078* (2013.01); *C07K 11/00* (2013.01); *A61K 38/00* (2013.01); *C07C 2601/14* (2017.05); *C07C 2602/42* (2017.05); *C07C 2602/44* (2017.05)

(58) Field of Classification Search
None
See application file for complete search history.

(56) References Cited

U.S. PATENT DOCUMENTS

| | | | |
|---|---|---|---|
| 3,745,212 A | 7/1973 | Benneville | |
| 4,339,534 A | 7/1982 | Johensen | |
| 2005/0070482 A1 | 3/2005 | Bachovchin | |
| 2007/0129314 A1 | 6/2007 | Bachovchin | |
| 2014/0288302 A1 | 9/2014 | Masuda et al. | |
| 2014/0303080 A1 | 10/2014 | Yu | |
| 2015/0057268 A1 | 2/2015 | Runyon | |

FOREIGN PATENT DOCUMENTS

| | | |
|---|---|---|
| CN | 101198584 A | 6/2008 |
| CN | 101519430 A | 9/2009 |
| CN | 101519431 A | 9/2009 |
| EP | 3440051 A1 | 2/2019 |
| JP | 2019513704 A | 5/2019 |
| WO | WO2001052900 A2 | 7/2001 |
| WO | 2005025554 A2 | 3/2005 |
| WO | 2007014258 A2 | 2/2007 |
| WO | 2017176461 A1 | 10/2017 |

OTHER PUBLICATIONS

Poleto "Aromatic Rings Commonly Used in Medicinal Chemistry: Force Fields Comparison and Interactions With Water Toward the Design of New chemical entities" Front Pharma 9(395):1-20 (Year: 2018).*
Vitaku "Analysis of the structural diversity, substitution patterns, and frequency of nitrogen heterocycles among U.S. FDA approved pharmaceuticals" J med chem 57(24):10257-74 (abstract only) (Year: 2014).*
Kirsch "BMP-2 antagonists emerge from alterations in the low-affinity binding epitope for receptor BMPR-II" EMBO 19(13):3314-3324 (Year: 2000).*
Cohen "Neuropeptide S in the basolateral amygdala mediates an adaptive behavioral stress response in a rat model of posttraumatic stress disorder by increasing the expression of BDNF and the neuropeptide YY1 receptor" Euro neuro psy pharma 28:159-170 (Year: 2018).*

(Continued)

*Primary Examiner* — Adam Weidner
(74) *Attorney, Agent, or Firm* — Barnes & Thornburg LLP

(57) ABSTRACT

Neuropeptide S receptor agonists are provided. The NPS agonists include peptidomimetic analogs exhibiting affinity for and activity at the neuropeptide S receptor. The molecules may be useful in the treatment of disorders, syndromes and conditions mediated by modulation of the neuropeptide S receptor such as substance abuse, narcolepsy, insomnia, obesity, cognitive decline, dementia, Alzheimer's disease, panic disorder, generalized anxiety, PTSD, phobias, schizophrenia and as supportive medication during any kind of cessation program in cognitive behavioral therapy, such as drug addiction, eating disorders and gambling.

22 Claims, No Drawings
Specification includes a Sequence Listing.

(56) References Cited

OTHER PUBLICATIONS

Zhao "Neuropeptide S Ameliorates Cognitive Impairment of APP/PS1 Transgenic Mice by Promoting Synaptic Plasticity and Reducing Ab deposition" front behav neuro 13(138):1-10 (Year: 2019).*
Zhang "Drug metabolism in drug discovery and development" acta pharma sinica b 8(5):721-732 (Year: 2018).*
International Search Report dated Jul. 4, 2017 for International Application No. PCT/US2017/023762 filed Mar. 23, 2017.
International Preliminary Report on Patentability dated Oct. 18, 2018 for International Application No. PCT/US2017/023762 filed Mar. 23, 2017.
Bernier et al., "Structure-function relationships in the neuropeptide S receptor: molecular consequences of the asthma-associated mutation N1071," J. Biol. Chem., 2006, vol. 281, No. 34, pp. 24704-24712.
Camarda et al., "Structure-activity study at positions 3 and 4 of human neuropeptide S," Biog. & Med. Chem., 2008, vol. 16, No. 19, pp. 8841-8845.
Camarda et al., "Synthesis and Biological Activity of Human Neuropeptide S Analogues Modified in Position 2," J. Med Chem., 2008, vol. 51, No. 3, pp. 655-658.
Guerrini et al., "Synthesis and Biological Activity of Human Neuropeptide S Analogues Modified in Position 5: Identification of Potent and Pure Neuropeptide S Receptor Antagonists," J. Med. Chem., 2009, vol. 52, pp. 524-529.
Roth et al., J. Biol Chem , "Structure-activity studies on neuropeptide S: identification of the amino acid residues crucial for receptor activation," 2006, vol. 281, No. 30, pp. 20809-20816.
Bergmann, M., et al., "Some synthetic and hydrolytic experiments with chymotrypsin", Journal of Biological Chemistry, (1938) vol. 124, No. 1, pp. 321-329.
Hays, A-M., et al., "Trapping of peptide-based surrogates in an artificially created channel of cytochrome c peroxidase", Protein Science, (2003) vol. 12, No. 2, pp. 278-287.
Hwang, G., et al., "5(4H)-oxazolinones as acyl donors in papain-catalyzed peptide fragment condensations", Tetrahedron Letters, (1994) vol. 35, No. 15, pp. 2317-2320.

Metrione, R.M., et al., "The enzymic condensation of a thiol ester-type carboxyl-activated acylamino acid with an amino acid amide to form a peptide", Biochemistry, (1963) vol. 3, No. 4, pp. 482-485.
RN: 1787583-13-4, ACD, STN CHEMCATS Registry Database.
Office Action for corresponding Chinese Application No. 2017800298864, dated Dec. 11, 2020.
Bluhm, L.H., et al., "An Alternative Procedure to Screen Mixture Combinatorial Libraries for Selectors for Chiral Chromatography", Anal. Chem. (2008), vol. 72, pp. 5201-5205.
Office Action for corresponding Japanese Application No. 2018-549269, dated Jan. 26, 2021.
Jungling, K., et al., "Neuropeptide S-mediated control of fear expression and extinction: role of intercalated GABAergic neurons in the amygdala", Neuron (Jul. 31, 2008), vol. 59, No. 2, pp. 298-310.
Lennertz, L., et al., "The functional coding variant Asn107Ile of the neuropeptides receptor gene (NPSR1) is associated with schizophrenia and modulates verbal memory and the acoustic startle response", International Journal of Neuropsychopharmacology (2012), vol. 15, pp. 1205-1215.
Okamura, N., et al., "Neuropeptide S enhances memory during the consolidation phase and interacts with Noradrenergic systems in the brain", Neuropsychopharmacology (2011), vol. 36, pp. 744-752.
Okamura, N., et al., "Gender-specific association of a functional coding polymorphism in the neuropeptide S receptor gene with panic disorder but not with schizophrenia or attention-deficit/hyperactivity disorder", Progress in Neuro-Psychopharmacology & Biological Psychiatry, (2007), vol. 31, pp. 1444-1448.
Si, W., et al., "Neuropeptide S stimujlates dopaminergic neurotransmission in the medial prefrontal cortex", J. Neurochem. (Oct. 2010), vol. 115, No. 2, pp. 475-482.
Xu, Y-L., et al., "Neuropeptide S: A neuropeptide promoting arousal and anxiolytic-like effects", Neuron, (Aug. 19, 2004), vol. 43, pp. 487-497.
Office Action dated Apr. 23, 2021 for corresponding EP Application No. 17 779 515.0.
Office action from corresponding Chinese Application 201780029886.4, dated Jul. 14, 2021.

* cited by examiner

NEUROPEPTIDE S RECEPTOR (NPSR) AGONISTS

CROSS-REFERENCE TO RELATED APPLICATIONS

This application is a National Stage application of International Application No. PCT/US2017/023762 filed Mar. 23, 2017, which claims benefit of priority to U.S. Provisional Application No. 62/318,042 filed Apr. 4, 2016. The disclosure of each related application is hereby incorporated herein by reference in its entirety.

This invention was made with government support under MH087826 awarded by the National Institutes of Health. The government has certain rights in the invention.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "15844-24_2018-10-02_Sequence_Listing.txt" created on Sep. 28, 2018, and is 4,096 bytes in size. The sequence listing contained in this .txt file is part of the specification and is hereby incorporated by reference herein in its entirety.

FIELD

The present disclosure relates to compounds specific for the neuropeptide S receptor, and which may be used in the treatment of a variety of diseases, syndromes and conditions. The present disclosure further relates to methods, compounds and compositions for selectively modulating the function of neuropeptide S receptors to provide pharmacotherapies capable of influencing conditions or disorders affected by the neuropeptide receptors.

DESCRIPTION OF THE RELATED ART

Neuropeptide S (NPS) is the endogenous ligand for the previous orphan G-protein-coupled receptor GPR154, now referred to as the neuropeptide S receptor (NPSR). Neuropeptide S is a 20-amino acid peptide that functions as an agonist through activation of its cognate $G_q$ or $G_s$ coupled, GPCR receptor system.

By way of selective neuropeptide S receptor activation, neuropeptide S regulates several biological functions including wakefulness, stress and anxiety, locomotor activity, food intake, memory processes, and drug abuse.

In view of the biological activity believed to be affected by NPS, the art is seeking compounds and compositions which provide activation of the desirable effects of NPS.

SUMMARY

The present disclosure relates to neuropeptide S (NPS) receptor agonists. In another aspect, the disclosure relates to a pharmaceutical composition comprising the NPSR agonists of Formulas I or II and a pharmaceutically acceptable carrier.

The neuropeptide S receptor agonists may be selected from neuropeptide S (NPS) receptor agonists according to one of Formula I or II:

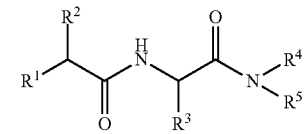

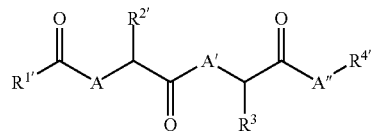

wherein $R^1$ is selected from H, phenyl, benzyl, benzyloxy, $C_2$-$C_4$ arylalkyl, $C_1$-$C_4$ alkylcycloalkyl, benzamido, polycyclic heterocycle, or branched or unbranched $C_1$-$C_6$ alkyl;
$R^2$ is selected from H, benzyl, or $C_2$-$C_4$ arylalkenyl; or $R^1$ and $R^2$ combine to form phenyl; provided that $R^1$ and $R^2$ are not both H;
$R^3$ is H or lysine side chain;
$R^4$ is a five membered saturated ring substituted with one —C(O)NH$_2$ group or a six membered saturated or aromatic ring substituted with one —C(O)NH$_2$ group, a heterocyclealkyl substituted with one —C(O)NH$_2$ group, $C_1$-$C_3$-amidoalkyl, a bridged bicyclic ring system substituted with one —C(O)NH$_2$ group, a cyclic imide, or —CH(Ph)-CH—C(O)NH$_2$, provided that if R' is benzamido, $R^4$ is either not a five membered saturated ring substituted with one —C(O)NH$_2$ group or a six membered saturated or aromatic ring substituted with one —C(O)NH$_2$ group, or $R^5$ is $C_1$-$C_3$-alkyl;
$R^5$ is H, $C_1$-$C_3$-alkyl, or benzyl;
$R^{1'}$ is phenyl;
$R^{2'}$ is benzyl;
A, A' and A" are independently selected from —NH— or —O—, provided that at least one of A, A' and A" is —O—;
$R^{4'}$ is a five membered saturated ring substituted with one C(O)NH$_2$ group or a six membered saturated or aromatic ring substituted with one C(O)NH$_2$ group;
or a pharmaceutically acceptable salt thereof.

In a further aspect, the disclosure relates to a method for treating a subject having a condition or disorder where modulation of neuropeptide S receptor activity is of therapeutic benefit, comprising administering to said subject having or susceptible to said condition or disorder a therapeutically effective amount of a compound according to Formula I or II.

Other aspects, features and embodiments of the disclosure will be more fully apparent from the ensuing description and appended claims.

DETAILED DESCRIPTION OF THE DISCLOSURE, AND PREFERRED EMBODIMENTS THEREOF

The present disclosure relates to neuropeptide S receptor agonists. The agonists of the disclosure include analogs exhibiting affinity for and activity at the neuropeptide S receptor. The molecules according to the disclosure may thus be useful in the treatment of disorders, syndromes and conditions mediated by modulation of the neuropeptide S receptor.

Human neuropeptide S (hNPS) is a 20 residue peptide with the primary sequence SFRNGVGTGMKKTSFQRAKS (SEQ ID NO: 1). Studies of the structure-function relationships in the neuropeptide S receptor have shown that the NH$_2$ terminal third of NPS, in particular residues Phe-2, Arg-3, Asn-4 and Val-6 are necessary and sufficient for activation of NPSR. Bernier et al., *J. Biol. Chem.*, 281(34): 24704-24712 (2006). According to this study, removal of the C-terminal 14 residues (peptide 1-6) has limited effect on the potency of the peptide, whereas removing Ser-1 (peptide 2-20) is detrimental to function and removing the first two (peptide 3-20) or three (peptide 4-20) NH$_2$-terminal residues results in largely inactive peptides. The study further stated that the results indicated that the first six residues, in particular residues Phe-2, Arg-3, Asn-4, and Val-6, are necessary for receptor activation, whereas residue Gly-7 is critically located and can modulate the inherent activity of the peptide.

According to another study, the effect of hNPS was mimicked by the fragment hNPS-(1-10), Phe-2, Arg-3 and Asn-4 are crucial for biological activity and the sequence Thr8-Gly9-Met10 is important for receptor activation. Roth et al., *J. Biol. Chem.*, 281(30):20809-20816 (2006). This study concluded that the sequence 1-10 was the smallest fragment able to activate the hNPSR with similar potencies and efficacies as full-length hNPS.

In view of these studies, other researchers have investigated the effects of making changes to various amino acids in the longer peptide hNPS, including structure activity studies at positions 3 and 4 of human neuropeptide S (Camarda et al., *Biog. & Med. Chem.* 16:8841-8845 (2008)), position 2 (Camarda et al., *J. Med Chem.* 51:655-658 (2008)) and position 5 (Guerrini et al., *J. Med. Chem.* 52:524-529, 4068-4071 (2009)).

The use of peptides as drugs may be limited by the following factors such as low metabolic stability towards proteolysis in the gastrointestinal tract and in serum, poor transport from the gastrointestinal tract to the blood and poor penetration into the central nervous system, among other issues. In view of the problems with using the full neuropeptide S ligand as a drug, the present disclosure provides small molecule compounds which offer activity at the neuropeptide S receptor. It has unexpectedly been found that the disclosed agonists of NPSR have effective potency and selectivity for the NPS receptor, despite earlier studies which indicated that truncated peptide structures would not be able to activate the hNPSR. In addition, it is believed that the disclosed agonists activate signaling pathway(s) in a manner enabling more selective treatment options that demonstrate reduced locomotor stimulation.

According to one aspect of the disclosure, a neuropeptide S (NPS) receptor agonist is provided according to one of Formula I or II:

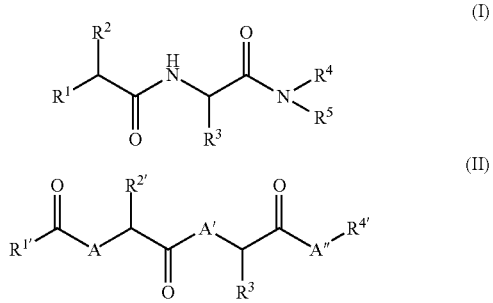

wherein R$^1$ is selected from H, phenyl, benzyl, benzyloxy, C$_2$-C$_4$ arylalkyl, C$_1$-C$_4$ alkylcycloalkyl, benzamido, polycyclic heterocycle, or branched or unbranched C$_1$-C$_6$ alkyl;

R$^2$ is selected from H, benzyl, or C$_2$-C$_6$ arylalkenyl; or R$^1$ and R$^2$ combine to form phenyl; provided that R$^1$ and R$^2$ are not both H;

R$^3$ is H or lysine side chain;

R$^4$ is a five membered saturated ring substituted with one C(O)NH$_2$ group or a six membered saturated or aromatic ring substituted with one C(O)NH$_2$ group, a heterocycleal-kyl substituted with one C(O)NH$_2$ group, C$_1$-C$_3$-amidoalkyl, a bridged bicyclic ring system substituted with one C(O) NH$_2$ group, a cyclic imide, or CH(Ph)-CH—C(O)NH$_2$, provided that if R$^1$ is benzamido, R$^4$ is either not a five membered saturated ring substituted with one C(O)NH$_2$ group or a six membered saturated or aromatic ring substituted with one C(O)NH$_2$ group, or R$^5$ is C$_1$-C$_3$-alkyl;

R$^5$ is H, C$_1$-C$_3$-alkyl, or benzyl;

R$^{1'}$ is phenyl;

R$^{2'}$ is benzyl;

A, A' and A" are independently selected from —NH— or —O—, provided that at least one of A, A' and A" is —O—;

R$^{4'}$ is a five membered saturated ring substituted with one C(O)NH$_2$ group or a six membered saturated or aromatic ring substituted with one C(O)NH$_2$ group;

or a pharmaceutically acceptable salt thereof.

Terms are used within their accepted meanings. The following definitions are meant to clarify, but not limit, the terms defined.

As used herein, the singular forms "a", "and", and "the" include plural referents unless the context clearly dictates otherwise.

As used herein, the identification of a carbon number range, e.g., in C$_1$-C$_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the disclosure.

Accordingly, C$_1$-C$_{12}$ alkyl is intended to include methyl, ethyl, propyl, butyl, pentyl, hexyl, heptyl, octyl, nonyl, decyl, undecyl and dodecyl, including straight chain as well as branched groups of such types, such as isopropyl and tert-butyl. It therefore is to be appreciated that identification of a carbon number range, e.g., C$_1$-C$_{12}$ or C$_1$-C$_6$, as broadly applicable to a substituent moiety, enables, in specific embodiments of the disclosure, the carbon number range to be further restricted, as a sub-group of moieties having a carbon number range within the broader specification of the substituent moiety. By way of example, the carbon number range e.g., C$_1$-C$_{12}$ alkyl, may be more restrictively specified, in particular embodiments of the disclosure, to encompass sub-ranges such as C$_1$-C$_4$ alkyl, C$_2$-C$_8$ alkyl, C$_2$-C$_4$ alkyl, C$_3$-C$_5$ alkyl, or any other sub-range within the broad carbon number range. Thus, for example, the range C$_1$-C$_6$ would be inclusive of and can be further limited by specification of sub-ranges such as C$_1$-C$_3$, C$_2$-C$_6$, C$_4$-C$_6$, etc. within the scope of the broader range.

"Alkenyl" refers to an unsaturated branched, straight-chain or cyclic alkyl group having at least one carbon-carbon double bond.

When the term "alkyl" or "alkenyl" is used as a suffix in conjunction with a second group, as in "arylalkyl", "hydroxyalkyl", "cycloalkylalkyl", "heterocyclealkyl" or "arylalkenyl" the second group is then connected to the rest of the molecule via an alkyl radical.

"Cycloalkyl" refers to an optionally substituted non-aromatic cyclic hydrocarbon ring. Unless otherwise indicated, cycloalkyl is composed of three to eight carbon atoms. Exemplary "cycloalkyl" groups include, but are not limited to, cyclopropyl, cyclobutyl, cyclopentyl, cyclohexyl, and cycloheptyl. The cycloalkyl group may be substituted or unsubstituted, for, example by a halogen, or a $C_1$-$C_3$-alkyl.

"Heterocycle" refers to saturated or unsaturated cyclic radicals containing one or more heteroatoms (e.g., O, N, S) as part of the ring structure and having two to seven carbon atoms, in the ring. In embodiments, a heterocycle may be fused to an aryl group such as phenyl. In such embodiments, the heterocycle may be fused to more than one aryl group. A polycyclic heterocycle refers to a cyclic radical having more than two cyclic rings, by way of example, three cyclic rings. The heterocycle or polycyclic heterocycle may be substituted or unsubstituted, for, example by a halogen, a carbonyl, or a $C_1$-$C_3$-alkyl.

"Heteroaryl" refers to unsaturated aromatic cyclic radicals containing one or more heteroatoms (e.g., O, N, S) as part of the ring structure and having two to seven carbon atoms in the ring. Heteroaryl groups may include furanyl, thienyl, pyridyl, pyrrolyl, pyrrolo, pyrimidyl, pyrazinyl, imidazolyl and the like. The heteroaryl group may be substituted or unsubstituted, for, example by a halogen, or a $C_1$-$C_3$-alkyl.

"Aryl" as used herein includes hydrocarbons derived from benzene or a benzene derivative that are unsaturated aromatic carbocyclic groups of from 6 to 10 carbon atoms. The aryls may have a single or multiple rings. One example is a phenyl group. The aryl group may be substituted or unsubstituted, for, example by a halogen, or a $C_1$-$C_3$-alkyl.

"Arylalkyl" refers to aryl-substituted alkyl radicals. Arylalkyl groups include benzyl and phenethyl.

"Alkylcycloalkyl" refers to cycloalkyl-substituted alkyl radicals.

The compounds of the disclosure may be further specified in specific embodiments by provisos or limitations excluding specific substituents, groups, moieties or structures, in relation to various specifications and exemplifications thereof set forth herein. Thus, the disclosure contemplates restrictively defined compositions, e.g., a composition wherein R is $C_1$-$C_{12}$ alkyl, with the proviso that R≠$C_i$ alkyl when $R^1$ is a specified molecular component, and i is a specific carbon number. The substituents maybe selected and combined with each other in any manner resulting in a compound according to Formula I or Formula II.

When chiral centers are present the stereochemistry of the structures includes both R and S configuration, unless otherwise indicated.

The disclosure, as variously set out herein in respect of various described features, aspects and embodiments, may in particular implementations be constituted as comprising, consisting, or consisting essentially of, some or all of such features, aspects and embodiments, as well as elements and components thereof being aggregated to constitute various further implementations of the disclosure. The disclosure contemplates such features, aspects and embodiments in various permutations and combinations, as being within the scope of the disclosure. The disclosure may therefore be specified as comprising, consisting or consisting essentially of, any of such combinations and permutations of these specific features, aspects and embodiments, or a selected one or ones thereof.

In one aspect of the disclosure, the neuropeptide S receptors are selected from the compounds represented by Formula I:

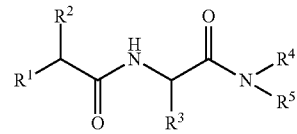

(I)

wherein $R^1$ is selected from H, phenyl, benzyl, benzyloxy, $C_2$-$C_4$ arylalkyl, $C_1$-$C_4$ alkylcycloalkyl, benzamido, polycyclic heterocycle, or branched or unbranched $C_1$-$C_6$ alkyl; $R^2$ is selected from H, benzyl, or $C_2$-$C_4$ arylalkenyl; or $R^1$ and $R^2$ combine to form phenyl; provided that $R^1$ and $R^2$ are not both H; $R^3$ is H, benzyl or lysine side chain; $R^4$ is a five membered saturated ring substituted with one $C(O)NH_2$ group or a six membered saturated or aromatic ring substituted with one $C(O)NH_2$ group, a heterocyclealkyl substituted with one $C(O)NH_2$ group, $C_1$-$C_3$ amidoalkyl, a bridged bicyclic ring system substituted with one $C(O)NH_2$ group, a cyclic imide, or —CH(Ph)-CH—$C(O)NH_2$, with the proviso that if R' is benzamido, $R^4$ is either not a five membered saturated ring substituted with one $C(O)NH_2$ group or a six membered saturated or aromatic ring substituted with one $C(O)NH_2$ group, or $R^5$ is $C_1$-$C_3$-alkyl; and $R^5$ is H, $C_1$-$C_3$-alkyl, or benzyl; or a pharmaceutically acceptable salt thereof.

In non-limiting embodiments, the aryl and the heterocycle are not substituted, or, if already substituted, are not further substituted. In other non-limiting embodiments, the heterocycle is a five or six membered ring including nitrogen. By way of example, the heterocycle may be connected to the alkyl chain via the nitrogen in the heterocycle group. By further way of example, the alkyl in the heterocylealkyl group is $C_1$-$C_3$ alkyl.

In other non-limiting embodiments, $R^1$ is phenyl, benzyl, benzyloxy or phenethyl; $R^2$ is benzyl; and $R^4$ is a six membered saturated ring substituted with one $C(O)NH_2$ group. In such embodiments, $R^3$ and $R^5$ may be H.

In other non-limiting embodiments, $R^1$ is phenyl or benzyl and $R^2$ is benzyl.

In other non-limiting embodiments, $R^1$ is benzamido, $R^2$ is benzyl, $R^4$ is $C_1$-$C_3$ amidoalkyl, more preferably, a carboxamide group such as —$CH(CH_2)CH_2C(O)NH_2$, or —CH(Ph)-CH—$C(O)NH_2$; and $R^5$ is H or benzyl.

In other non-limiting embodiments, $R^1$ is benzamido, $R^2$ is benzyl, $R^4$ is a six membered saturated ring (i.e., cyclohexane) substituted with one $C(O)NH_2$, and $R^5$ is methyl. In such embodiments, $R^3$ may be H.

In other non-limiting embodiments, $R^1$ is H or phenethyl, $R^2$ is $C_1$-$C_3$ arylalkenyl, and $R^4$ is a six membered saturated ring substituted with one $C(O)NH_2$.

In other non-limiting embodiments, $R^1$ is $C_1$-$C_4$-alkylcycloalkyl, more preferably $CH_2CH_2$-cyclohexyl, or branched or unbranched $C_1$-$C_6$-alkyl, more preferably isopentyl, $R^2$ is benzyl and $R^4$ is a six membered saturated ring substituted with one $C(O)NH_2$. In such embodiments, $R^3$ and $R^5$ may be H.

In other non-limiting embodiments, $R^1$ is phenethyl, $R^2$ is benzyl, $R^3$ is H or lysine side chain, and $R^4$ is a five membered saturated ring (i.e., cyclopentane) substituted with one $C(O)NH_2$ group or a six membered saturated or aromatic ring substituted with one $C(O)NH_2$ group, a heterocyclealkyl substituted with one C(O)NH₂ group, or a bridged bicyclic ring system substituted with one C(O)NH₂ group. By way of example, the bicyclic ring system may be bicyclo[2.2.2]octane or bicyclo[2.2.1]heptane.

In non-limiting embodiments, the cyclic imide is succinimido.

In other non-limiting embodiment, the polycyclic heterocycle is a heterocycle fused to an aryl group. In certain embodiments, the polycyclic heterocycle is represented by the formula below:

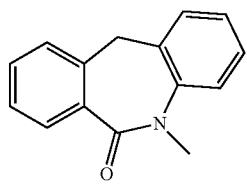 [SMILES: CN1C(=O)c2ccccc2Cc2ccccc21]

Representative neuropeptide S receptor agonists of Formula I include the following:

R06039-641

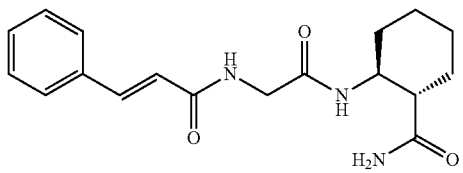

R06039-642

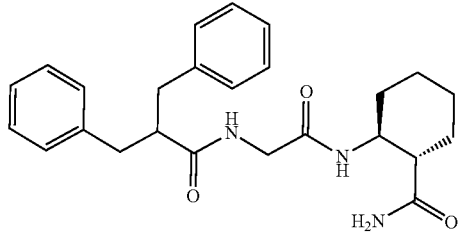

R06039-644

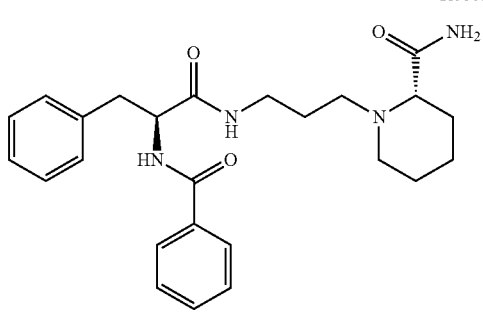

R06039-655

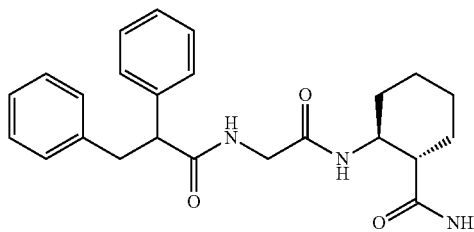

R06039-656

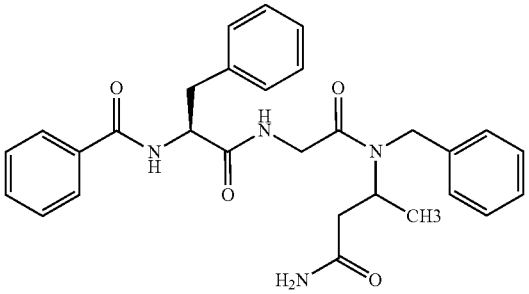

R06039-657

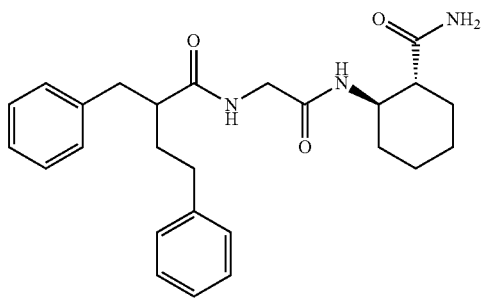

R06039-658

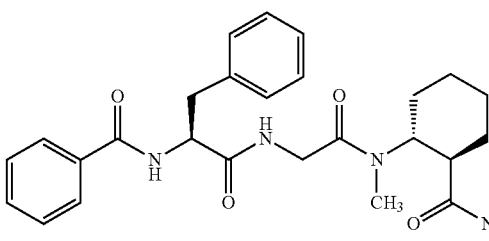

R06039-662

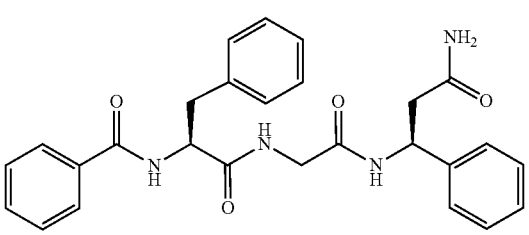

R06039-663

-continued
R06039-675
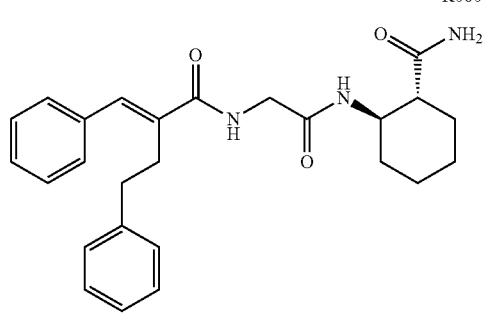
R06039-682
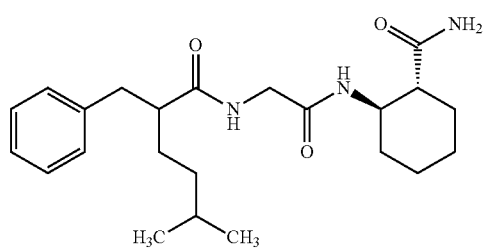
R06039-686
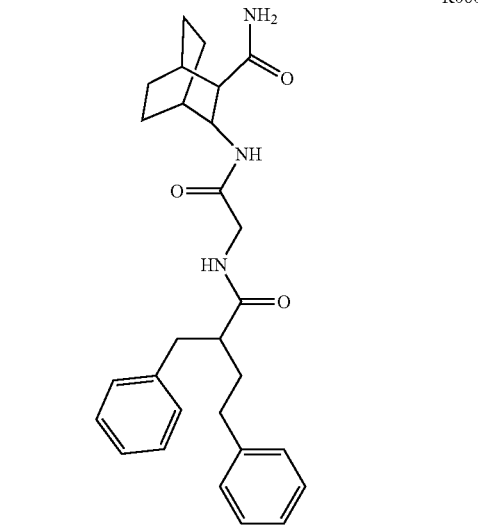
R06039-691
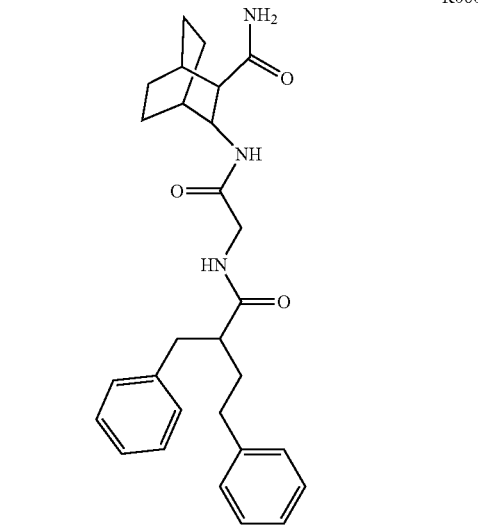
-continued
R06039-692
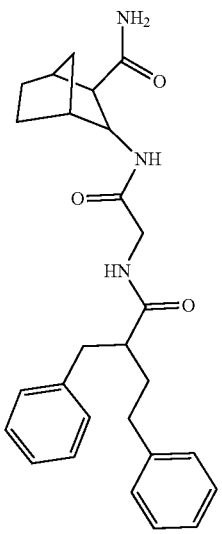
R06039-693
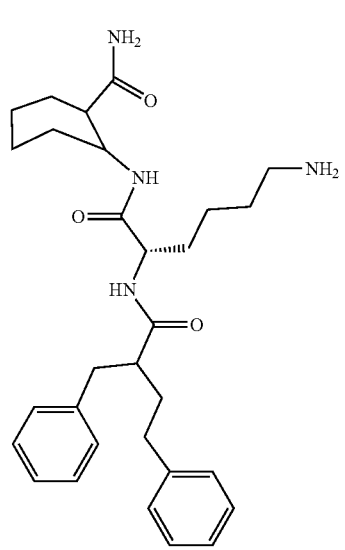
R06039-694
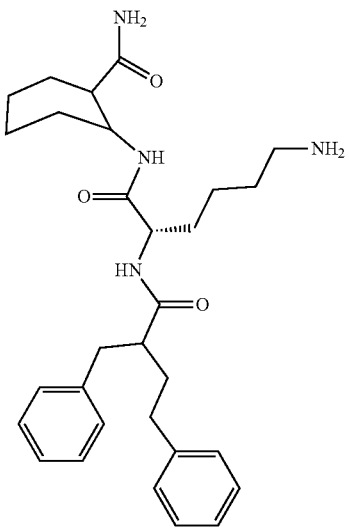

R06039-695
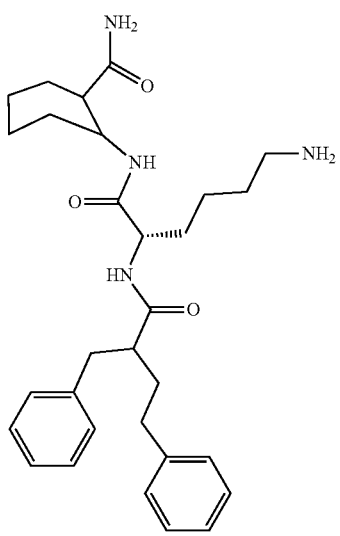
R06039-696
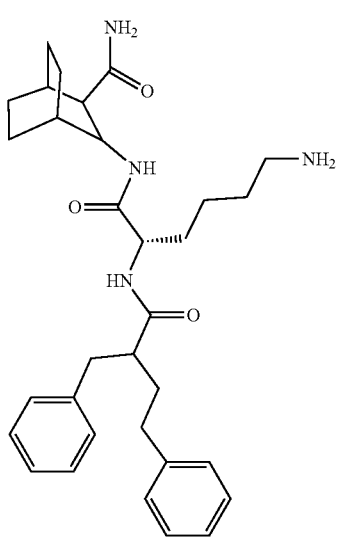
R06039-697
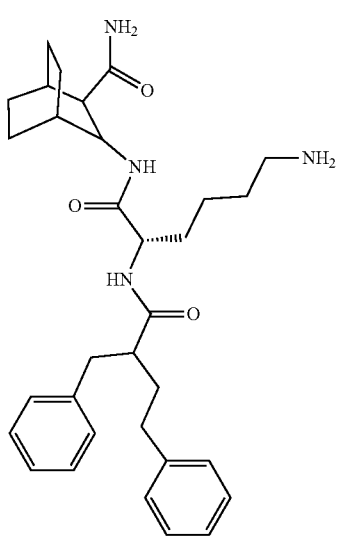
R06039-698
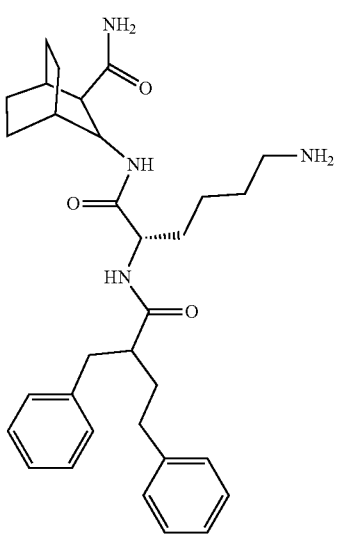
R06039-522
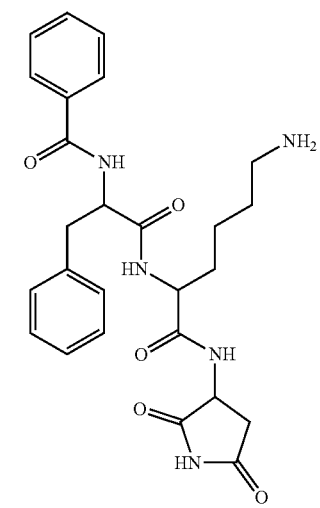
R06039-715
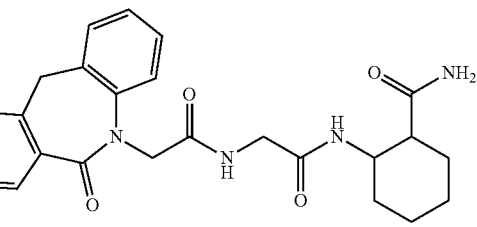
In another aspect of the disclosure, the neuropeptide S receptors are selected from the compounds represented by Formula II:
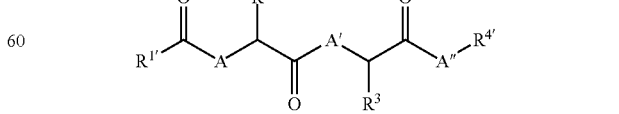
(II)
wherein $R^{1'}$ is phenyl;
$R^{2'}$ is benzyl;
A, A' and A'' are independently selected from —NH— or —O—, provided that at least one of A, A' and A'' is —O—;

R³ is H, benzyl or lysine side chain;
R⁴' is a five membered saturated ring substituted with one C(O)NH₂ group or a six membered saturated or aromatic ring substituted with one C(O)NH₂ group;
or a pharmaceutically acceptable salt thereof.

In non-limiting embodiments, R⁴' of Formula II is a six membered saturated ring (i.e., cyclohexane) substituted with one C(O)NH₂ group.

Representative neuropeptide S receptor agonists of Formula II include the following:

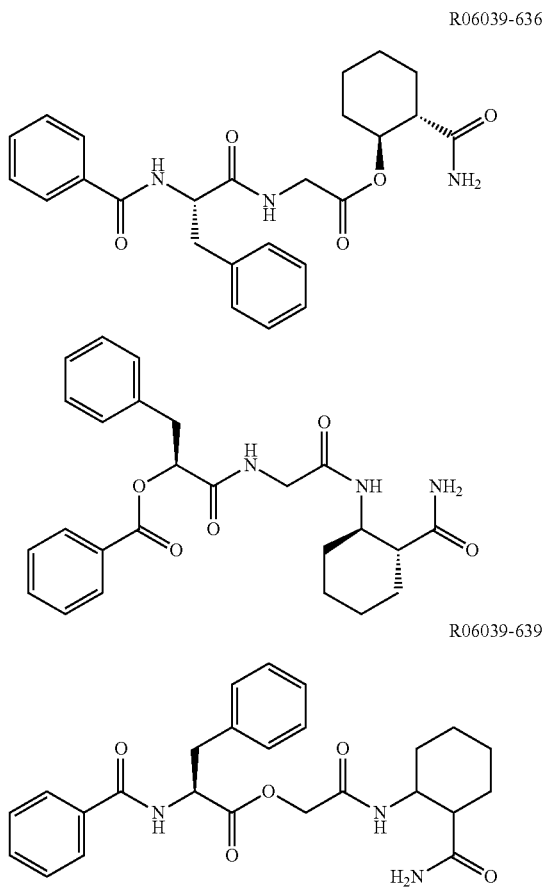

The compounds of the disclosure have full and partial agonist activity for the NPS receptor. EC50 values range from 14-3544 nM.

The neuropeptide S receptor has at least three known isoforms including the wild type NPS Asn¹⁰⁷, the NPS Asn107Ile and NPS C-Alt. Since each variant could potentially have functional difference, the agonist sensitivity of each isoform was evaluated. Radioligand binding of [¹²⁵I] Tyr¹⁰-NPS was unaltered among receptor variants; however, a 5-10 fold enhancement in functional sensitivity using calcium flux was observed for the Ile¹⁰⁷ variant over Asn¹⁰⁷. In a functional assay, hNPS was the least potent at NPSR-C-Alt (30-fold lower versus the 1071 variant).

In situ hybridization has shown that NPS receptor mRNA was expressed widely throughout the CNS. In particular, high levels of NPS receptor mRNA were identified in the thalamus, hypothalamus, cortex, hippocampus, and amygdala. Human NPS precursor mRNA, however, is largely expressed in the locus ceruleus (LC) of the brainstem and is cleaved from an 89 AA signal peptide at a specific cleavage site adjacent to the amino acids Arg Lys. Due to mRNA localization in the LC, NPS was hypothesized to play a role in arousal, anxiety, or both. The arousal and anxiolytic promoting properties of NPS has since been confirmed using stress-induced hypothermia. In view of these properties, the NPS receptor system may be useful as a target for non-sedating anxiolytics.

Other studies have found evidence for the role NPS plays in the sleep-wake cycle and a specific association between usual bedtime and the NPS N1071 SNP was discovered. Thus, NPS pharmacotherapies may benefit patients suffering from insomnia or narcolepsy.

NPSR mRNA is expressed at very high levels in hippocampal areas known for regulating learning and memory such as the endopiriform cortex/nucleus and the subiculum. Therefore, NPS may be involved in memory and the consolidation of memory. NPS administration dose-dependently improved performance in novel recognitions assays, confirming a biochemical role in memory.

NPS is also implicated in the induction of acute anxiolytic-like effects in addition to the simultaneous reduction in the consolidation of aversive memories. NPS was found to be involved in mitigating fear expression as opposed to inhibiting fear learning. Thus, the activation of the NPS receptor has been found to possess a dual role in mitigating anxiety. In addition to the acute effects NPS has on anxiety, the more important role of facilitating extinction of aversive memories has been identified. The NPS agonist compounds and compositions of the disclosure may thus be useful to effectively treat anxiety and anxiety-related disorders such as post-traumatic stress disorder (PTSD).

In one aspect of the disclosure, methods of treating a variety of disorders and conditions modulated by the neuropeptide S receptor are provided. The NPS receptor agonists of the disclosure may be useful for substance abuse, narcolepsy, insomnia, obesity, cognitive decline, dementia, Alzheimer's disease, panic disorder, generalized anxiety, PTSD, phobias, schizophrenia and as supportive medication during any kind of cessation program in cognitive behavioral therapy, by way of example, such as drug addiction, eating disorders and gambling.

The term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

In one aspect of the disclosure, the compounds and compositions of the disclosure may be used in combination with other drugs or agents, or in conjunction with a variety of psychotherapies useful in the treatment of the type of conditions and disorders modulated by the NPS receptor. Drugs or agents which may be used with the compounds and compositions of the disclosure may include typical and/or atypical antipsychotics such as haloperidol and aripiperazole or monoamine reuptake inhibitors such as fluoxetine and sertraline.

In another aspect of the disclosure, a method for treating a subject having a condition or disorder where modulation of neuropeptide S receptor activity is of therapeutic benefit is provided, the method comprising administering to said subject having or susceptible to said condition or disorder an effective amount of a compound demonstrating selective binding for a neuropeptide S receptor and exhibiting functional agonist activity for a neuropeptide S receptor.

In one aspect of the disclosure, a method is provided for treating a subject having a condition or disorder where modulation of neuropeptide S receptor activity is of therapeutic benefit comprising administering to said subject having or susceptible to said condition or disorder an effective amount of a compound according to one of Formulas I or II demonstrating selective binding and functional agonist activity at a neuropeptide S receptor. The NPS receptor selectivity may be determined based on the binding affinities at the receptors indicated or their selectivity in NPS functional assays.

In embodiments, the compound administered is a pharmaceutically acceptable salt of any compound of the foregoing formulas. In this aspect, any of the compounds of Formulas I or II may be combined with a pharmaceutically acceptable carrier.

Salts of the compounds of the present disclosure may be made by methods known to a person skilled in the art. The acid may be an inorganic acid or an organic acid. Suitable acids include, for example, hydrochloric, hydroiodic, hydrobromic, sulfuric, phosphoric, citric, acetic and formic acids.

A variety of administration techniques may be utilized, among them oral, transdermal or parenteral techniques such as subcutaneous, intravenous, intraperitoneal, intracerebral and intracerebroventricular injections, catheterizations and the like. Such methods of administration are well-known to those skilled in the art. For a general discussion of drug delivery systems and administration modalities, see Kirk-Othmer Encyclopedia of Chemical Technology, Fourth Edition, Volume 8, pp. 445-475.

Average quantities of the compounds may vary in accordance with the binding properties of the compound (i.e., affinity, onset and duration of binding) and in particular should be based upon the recommendations and prescription of a qualified physician.

The therapeutic compositions useful in practicing the therapeutic methods of this disclosure may include, in admixture, a pharmaceutically acceptable excipient (carrier) and one or more of the compounds of the disclosure, as described herein as an active ingredient.

The NPS receptor agonists of the disclosure may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including Silastic™ and biodegradable implants, skin patches, skin creams, or intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the disclosure contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol (e.g., polyoxyethylene sorbitol mono-oleate), or a condensation product of ethylene oxide with a partial ester derived from a fatty acid and a hexitol anhydride (e.g., polyoxyethylenesorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the disclosure suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitolamhydrides, such as sorbitan mono-oleate, and condensation products of these partial esters with ethylene oxide, such as polyoxyethylenesorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as, for example, by aseptic filtration, or irradiation.

Aqueous formulations (i.e oil-in-water emulsions, syrups, elixirs and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this disclosure may also be administered in the form of suppositories for rectal administration of the drug. These compositions can be prepared by mixing the drug with a suitable nonirritating excipient which is solid at ordinary temperatures but liquid at rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

Products of the disclosure which are preferably administered by the topical route may be administered as applicator sticks, solutions, suspensions, emulsions, gels, creams, ointments, pastes, jellies, paints, powders, and aerosols.

The advantages and features of the disclosure are further illustrated with reference to the following example, which is not to be construed as in any way limiting the scope of the disclosure but rather as illustrative of one embodiment of the disclosure in a specific application thereof.

EXAMPLES

Scheme 1: Synthesis of Trans 2-(2-(2-benzyl-4-phenylbutanamido) acetamido) cyclohexane carboxamide (R06039-644)

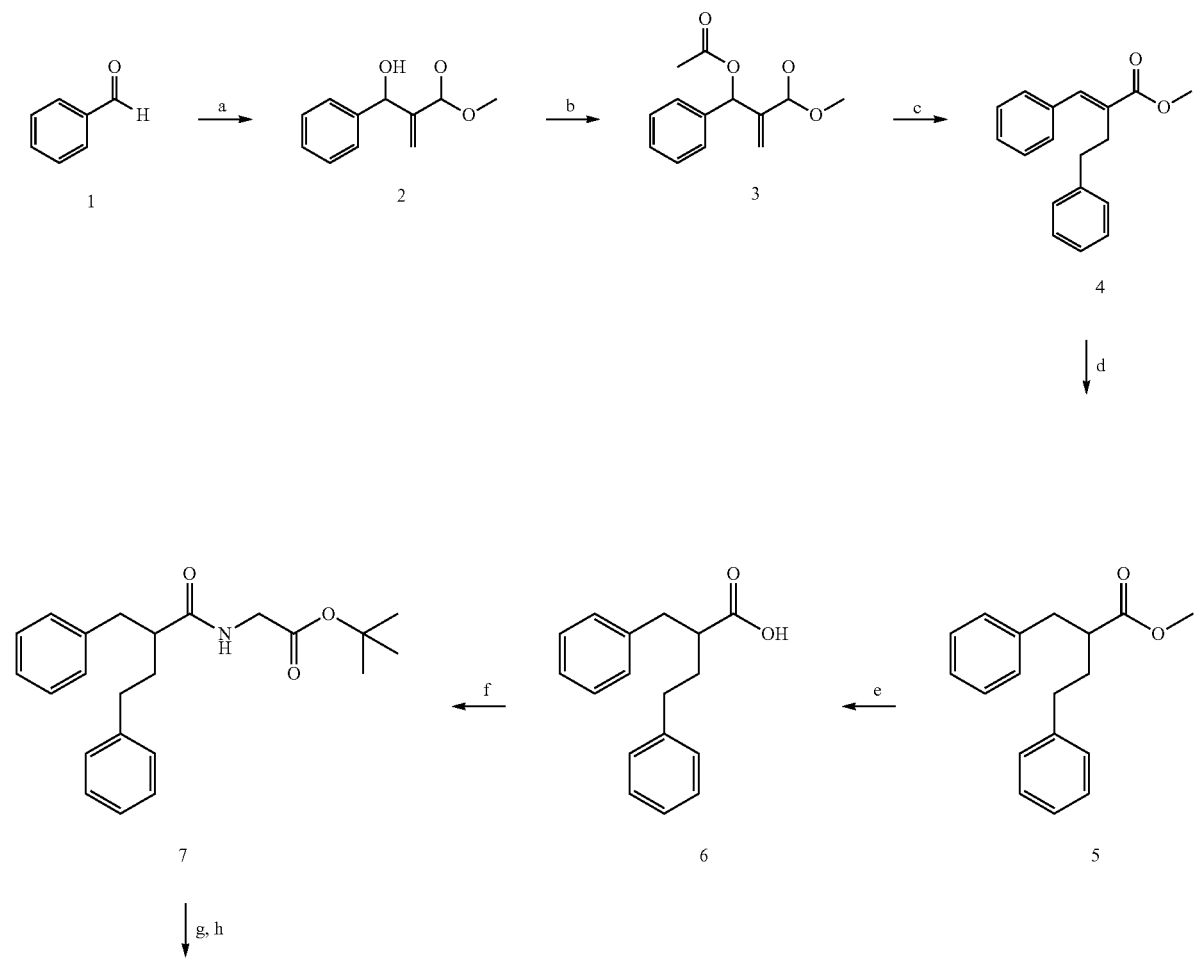

-continued

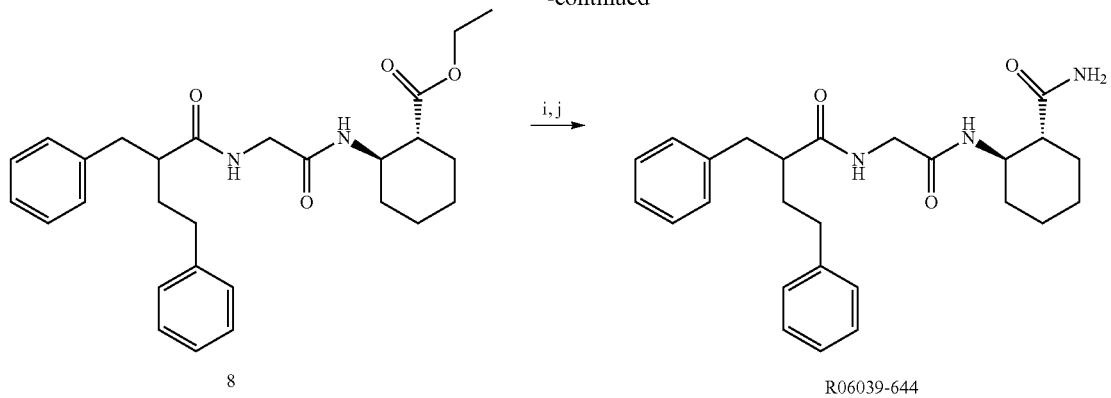

Reagents and conditions: (a) Methyl acrylate, DABCO, MeOH, 0° C., 48 h, 87%; (b) acetyl chloride, pyridine, 0° C., 1.5 h; 92% (c) Benzyl magnesium chloride (1M ether solution), diethyl ether, -40° C. to -5° C., 3 h; 77% (d) 10% Pd/C, MeOH, 45 psi, 4 hr, 94%; (e) LiOH, MeOH, THF, H₂O, rt, 3 h; (f) Glycine tert-butyl ester hydrochloride, BOP, Et₃N, rt, 3 h, 76%; (g) TFA, CH₂Cl₂, rt, 4 h; 76%; (h) ethyl trans-2-amino-1-cyclohexane, EDC. HCl, CH₂Cl₂, rt, 16 h, 60%; (i) LiOH, THF, MeOH, H₂O, rt, 3 h; 28%; (j) 0.5M NH₃ in THF, BOP, Et₃N, rt, 3 h, 76%.

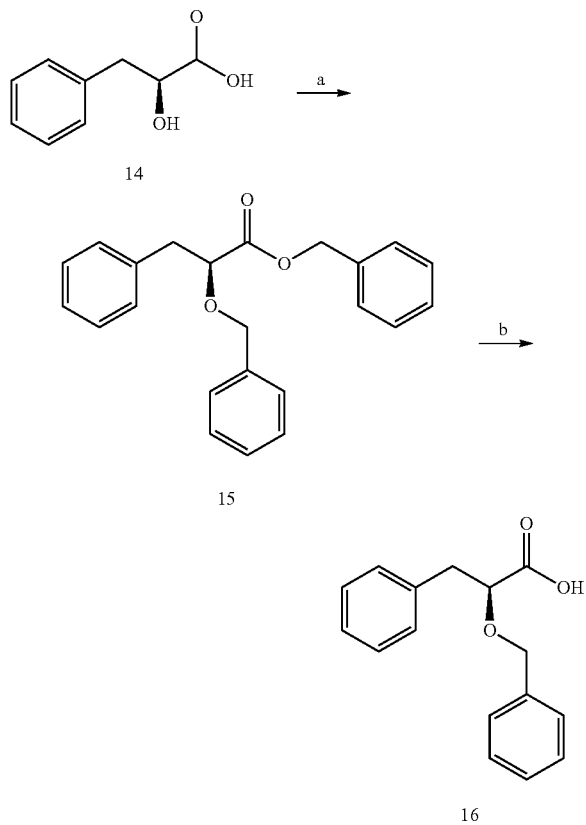

Scheme 2. Synthesis of R06039-641 intermediates.

Reagents and conditions: (a) Benzyl bromide, Ag₂O, CH₃CN, 60° C., 16 h, 65%; (b) 6N HCl, 1,4-dioxane, 60° C., 24 h; 58%

Experimental Section

Abbreviations used for amino acids and designation of peptides follow the rules of the IUPAC-IUB Commission of Biochemical Nomenclature in J. Biol. Chem. 1972, 247, 977-983. Amino acid symbols denote L-configuration unless indicated otherwise. The following additional abbreviations are used: aq, aqueous; Boc, tert-butyloxycarbonyl; tBu, tert-butyl; DCM, dichloromethane; DIEA, N,N-diisopropylethylamine; DMF, N,N-dimethylformamide; Fmoc, 9-fluorenylmethoxycarbonyl; ESI MS, electron spray ionization mass spectrometry; equiv, equivalent; Fmoc-trans-ACHC, Fmoc-trans-(1R/S,2R/S)-2-aminocyclocyclohexanecarboxylic acid ELSD, electron light scattering ESI-MS electron spray mass spectroscopy; h, hour; HOBt, N-hydroxybenzotriazole; HBTU, 2-(1H-benzotriazole-1-yl)-1,1,3,3-tetramethyluronium hexafluorophosphate; meq, mole equivalent; Mtt, monomethoxytriphenylmethyl; NMR, nuclear magnetic resonance spectroscopy; RP-HPLC, reversed-phase high performance liquid chromatography; rt, room temperature; TFA, trifluoroacetic acid; TFE, trifluoroethanol; TIPS, tris-iso-propylsilane; Trt, triphenylmethyl (trityl), tR, retention time.

General: All standard reagents were commercially available. Compounds were purified by HPLC on an Agilent-Varian HPLC system equipped with Prostar 210 dual pumps, a Prostar 335 Diode UV detector and a SEDEX75 (SEDERE, Olivet, France) ELSD detector. The HPLC solvent system was binary, water containing 0.1% trifluoroacetic acid (TFA) and solvent B (acetonitrile containing 5% water and 0.1% TFA). A semi-preparative Synergy Hydro® RP 80A C18 column (4 μm 250×21.2 mm column; Phenomenex) was used to purify final compounds at 15 mL/min using a linear gradient from 5% to 50% B over 20 min. Absorbance was monitored at 220 nm. The purity of final compounds was determined using an analytical Synergy Hydro® RP80A C18 (4 μm 250×4.60 mm column; Phenomenex) with a linear gradient of 5%-95% solvent B over 20 min at a flow rate of 1 mL/min. Absorbance was monitored at 220 nm. The molecular ion of final compounds was determined using a PE Sciex API 150 EX LC/MS system from Perkin Elmer (San Jose, Calif.). ¹H NMR spectra were recorded at 300 MHz on a Bruker Avance 300 Spectrospin instrument and are reported as follows: chemical shift d in ppm (multiplicity, coupling constant (Hz), and integration. The following abbreviations were used to explain multiplicities: s=singlet, d=doublet; m=multiplet, br=broad, dd=doublet of doublets.

Synthesis. Materials. Nα-Fmoc-protected amino acids, HBTU and HOBt were purchased from AAPPTEC (Louisville, Ky.) and from Chem-Impex International Inc. (Wooddale, Ill.). Trityl resin was purchased from AnaSpec (Fremont, Calif.). Rink resin was purchased from Chem-Impex (Wood Dale, Ill.). Peptide synthesis solvents, reagents, as well as CH$_3$CN for HPLC were acquired from commercial sources and used without further purification. The synthesis of NPS analogues was performed in part or completely on solid-phase resin method in a stepwise fashion via peptide synthesizer (AAPPTEC Focus XC, AAPPTEC). Nα-Fmoc-AA1-OH (AA1: Fmoc-trans-ACHC, Nα-Fmoc-(S)-cyanoalanine, Nα-Fmoc-(S)-β-tetrazolealanine, Nα-Fmoc-Nε-Boc-(S)-lysine or Nβ-Fmoc-(S)-3-amino-3-phenylpropanoic acid was coupled to Rink resin (0.52 meq/g) via peptide coupling or coupled to Trityl resin (0.1 g, 0.9 meq/g) with DIEA (2M in NMP) for 90 min. The following protected amino acids were then added stepwise Nα-Fmoc-AA2-OH (AA2: Fmoc-Gly-OH, Nα-Fmoc-Nε-Boc-(S)-lysine, Nα-Fmoc-Nε-Mtt-(S)-lysine or Nα-Fmoc-Phe-OH). Each coupling reaction was accomplished using a 3-fold excess of amino acid with HBTU and HOBt (1.5 mL, 0.5M each in DMF) in the presence of DIEA (0.8 mL, 2M in NMP). The Nα-Fmoc protecting groups were removed by treating the protected peptide resin with a 20% solution of piperidine in DMF, (1×5 min, 1×10 min).

The peptide resin was washed three times with DMF and the next coupling step was initiated in a stepwise manner. All reactions were performed under an N$_2$ atmosphere. The peptide resin was washed with DMF (3×) and the deprotection protocol was repeated after each coupling step. The N-terminal Fmoc group was removed as described above, the resin washed with DMF (3×) and DCM (3×), and the peptide was released from the resin with acetic acid/TFE/DCM (1:1:8, 10 mL) over 20 min., or TFA/TIPS/H$_2$O (95:2.5:2.5) over 1.5 h, or TFA/DCM (1:1, 5 mL) over 0.5 h. The resin was removed by filtration and the crude peptide was recovered by precipitation with cold anhydrous ethyl ether to give a white powder which was used crude or purified by semi-preparative RP-HPLC using a gradient of CH$_3$CN in 0.5% aqueous TFA (from 5 to 90% in 30 min unless otherwise indicated) at a flow rate of 15.0 mL/min. The product was obtained by lyophilization of the appropriate HPLC fractions. Analytical RP-HPLC indicated a purity of >90% and molecular weights were confirmed by ESI-MS.

Synthesis of R06039-584

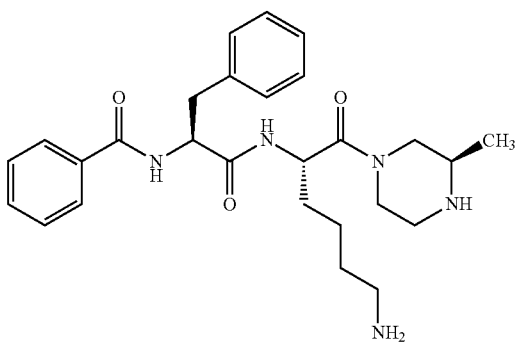 [SMILES: C[C@@H]1CN(C(=O)[C@H](CCCCN)NC(=O)[C@H](Cc2ccccc2)NC(=O)c2ccccc2)CCN1]

N—((S)-1-((S)-6-amino-1-((R)-3-methylpiperazin-1-yl)-1-oxohexan-2-ylamino)-1-oxo-3-phenylpropan-2-yl)benzamide TFA salt (R06039-584)

Nα-Fmoc-Nε-Boc-(S)-lysine was coupled to Trityl resin (200 mg, 0.9 meq/g) with DIEA (2M in NMP) for 90 min using an AAPPTEC Focus peptide synthesizer. The amino acid on resin was washed with DMF (5×10 mL) and the Nα-Fmoc protecting group removed with a 20% solution of piperidine in DMF, (1×5 min, 1×10 min) followed by DMF wash (3×). Nα-Fmoc-Phe-OH was added using a 3-fold excess of amino acid with HBTU and HOBt (1.5 mL, 0.5M each in DMF) in the presence of DIEA (0.8 mL, 2M in NMP) under nitrogen atmosphere over 45 min. The Nα-Fmoc protecting group was removed by treating the protected peptide resin with a 20% solution of piperidine in DMF, (1×5 min, 1×10 min). The peptide resin was washed three times with DMF and then coupled with benzoic acid (3 equivalents) with HBTU and HOBt (1.5 mL, 0.5M each in DMF) in the presence of DIEA (0.8 mL, 2M in NMP) under nitrogen atmosphere over 45 min. The peptide resin was washed with DMF (3× and DCM (3×), and the peptide was released from the resin with acetic acid/TFE 1 DCM (1:1:8, 10 mL) over 1 h. The resin was removed by filtration and the crude peptide was recovered by precipitation with cold anhydrous ethyl ether to provide (3S,6S)-3-benzyl-14,14-dimethyl-1,4,12-trioxo-1-phenyl-13-oxa-2,5,11-triazapentadecane-6-carboxylic acid (Benzoyl-(S)-phenylalanine-Nε-Boc-(S)-lysine) TFA salt (benzoyl-(S)-phenylalanine-Nε-Boc-(S)-lysine, 89 mg, 93%) as a white powder. The material was used without further purification in the subsequent solution phase coupling.

To a solution of (3S,6S)-3-benzyl-14,14-dimethyl-1,4,12-trioxo-1-phenyl-13-oxa-2,5,11-triazapentadecane-6-carboxylic acid TFA salt (benzoyl-(S)-phenylalanine-Nε-Boc-(S)-lysine), 50 mg, 0.1 mmol), HBTU (57 mg, 0.15 mmol), HOBt (23 mg, 0.15 mmol), and (R)-Boc-2-methylpiperazine (40 mg, 0.2 mmol) was added DIPEA (70 mL, 0.4 mmol), and the reaction mixture stirred at room temperature overnight. The reaction mixture was concentrated, re-dissolved in methanol (2 mL) and cooled to 0° C. A 1 N solution of HCl in diethylether (1.5 mL, 1.5 mmol) was added, the reaction mixture was stirred at room temperature overnight and concentrated to dryness. The residue was purified by semi-preparative RP-HPLC using a gradient of CH$_3$CN in 0.5% aqueous TFA (from 5 to 95% in 20 min) at a flow rate of 15.0 mL/min. The desired product was obtained as the TFA salt (R06039-584: 13.3 mg, 28%). NMR (300 MHz, DMSO-d$_6$) d ppm 1.12-1.42 (m, 5H) 1.43-1.77 (m, 6H) 2.76 (d, J=7.54 Hz, 1H) 2.89-3.15 (m, 3H) 3.18-3.39 (m, 2H) 3.91 (d, J=16.20 Hz, 1H) 4.15 (d, J=12.81 Hz, 2H) 4.40 (d, J=12.06 Hz, 1H) 4.69 (d, J=10.55 Hz, 2H) 7.11-7.57 (m, 8H) 7.69 (br. s., 2H) 7.73-7.84 (m, 2H) 8.47 (br. s., 1H) 8.59 (dd, J=13.37, 8.10 Hz, 1H) 8.88 (br. s., 1H) 9.11 (br. s., 1H); ESI MS m/z: Calculated for C$_{27}$H$_{37}$N$_5$O$_3$ 479.61, Found 480.4 (M+H)$^+$; HPLC (Synergy Hydro, 20 min) t$_R$=11.89 min (>99.9%).

Synthesis of R06039-636
(1S,2S)-2-hydroxycyclohexanecarboxamide (1R,2S)-2-hydroxycyclohexanecarbonitrile (250 mg, 2 mmol) was placed in concentrated hydrochloric acid (4 mL) and stirred at 55° C. for 2.5 hours. The mixture was allowed to cool to room temperature and then cooled to 0° C. Sodium hydroxide solution (10N, 3.5 mL) was added, followed by saturated sodium bicarbonate solution to adjust the pH of the solution to 8-9. The solution was then extracted several times with a mixture of dichloromethane/THF (70:30). The organic layers were combined and the solvent removed under reduced pressure. The residue was taken up in a mixture of dichloromethane/THF (70:30), stirred for 30 minutes and filtered. The filtrate was dried over sodium sulfate and the solvent was removed under reduced pressure. The residue was vacuum dried to give (1S,2S)-2-hydroxycyclohexanecarboxamide as a white solid that was used without further purification (166 mg, 58.0%). NMR (300 MHz, METHANOL-$d_4$) d ppm 1.11-1.57 (m, 4H) 1.64-1.82 (m, 2H) 1.87 (d, J=13.00 Hz, 1H) 1.93-2.06 (m, 1H) 2.07-2.22 (m, 1H) 3.54-3.78 (m, 1H) 4.46-4.79 (m, 1H).

(1S,2S)-2-carbamoylcyclohexyl-2-[(2S)-3-phenyl-2-(phenylformamido)propanamido]acetate (RO6039-636)

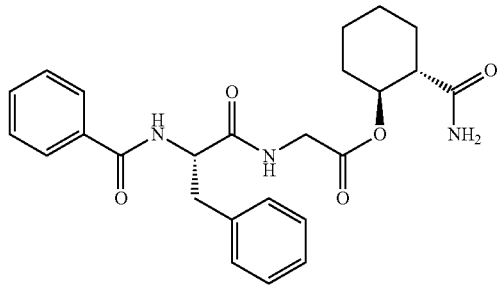 [SMILES: NC(=O)[C@H]1CCCC[C@@H]1OC(=O)CNC(=O)[C@H](Cc1ccccc1)NC(=O)c1ccccc1]

N-(phenylcarbonyl)-L-phenylalanylglycine (95 mg; 0.291 mmol), (1S,2S)-2-hydroxycyclohexanecarboxamide (34 mg, 0.237 mmol) and DCC (60 mg, 0.291 mmol) were dissolved in dichloromethane (5 mL) and the mixture cooled to 0° C. in a ice bath. DMAP (30 mg, 0.246 mmol) was added and the mixture stirred at 0° C. for one hour. The solution was allowed to warm to room temperature and stir overnight. The solution was filtered and the precipitate subsequently washed well with ether/dichloromethane (50/50) and vacuum dried to give a white solid (16 mg). The solvent was removed from the filtrate and the residue dissolved in dichloromethane. The solution was then washed with 0.1N HCl and the organic layer dried over sodium sulfate. The solvent was removed under reduced pressure and the residue purified by purified by preparative thin layer chromatography (silica, 20×20 cm plate, 1000 microns, THF). The purified material was then dissolved in dichloromethane and precipitated with hexane. The resulting solid was vacuum dried to give RO6039-636 (33 mg; 49 mg total; 45.7%). $^1$H NMR (300 MHz, DMSO-$d_6$) d ppm 0.99-1.49 (m, 4H) 1.53-1.73 (m, 2H) 1.80 (d, J=11.11 Hz, 1H) 1.95 (d, J=9.04 Hz, 1H) 2.21-2.39 (m, 1H) 2.92-3.07 (m, 1H) 3.08-3.22 (m, 1H) 3.64-3.96 (m, 2H) 4.65-4.89 (m, 2H) 6.78 (s, 1H) 7.09-7.20 (m, 1H) 7.21-7.30 (m, 2H) 7.31-7.55 (m, 6H) 7.72-7.84 (m, 2H) 8.51 (t, J=5.84 Hz, 1H) 8.62 (d, J=8.48 Hz, 1H). ESI MS m/z: Calculated for $C_{25}H_{29}N_5O_3$ 451.51, Found 452.5 (M+H)+.

(S)-1-(2-((1R/S,2S/R)-2-carbamoylcyclohexylamino)-2-oxoethylamino)-1-oxo-3-phenylpropan-2-yl benzoate (RO6039-637)

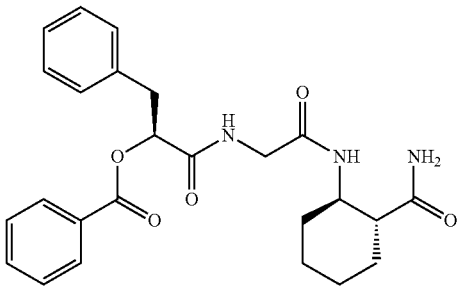 [SMILES: NC(=O)[C@@H]1CCCC[C@H]1NC(=O)CNC(=O)[C@H](Cc1ccccc1)OC(=O)c1ccccc1]

Fmoc-trans-(1R/S,2R/S)-2-aminocyclocyclohexanecarboxylic acid was coupled to Rink resin (0.52 meq/g) via peptide coupling using an AAPPTEC Focus peptide synthesizer. Rink resin (130 mg) was washed with DMF (5×10 mL) and the Nα-Fmoc protecting group removed with a 20% solution of piperidine in DMF, (1×5 min, 1×10 min) followed by DMF wash (3×). The following protected amino acids were then added stepwise Nα-Fmoc-AA2-OH (AA2: Nα-Fmoc-Gly-OH, Nα-Fmoc-Phe-OH). Each coupling reaction was accomplished using a 3-fold excess of amino acid with HBTU and HOB ((1.5 mL, 0.5M each in DMF) in the presence of DIEA (0.8 mL, 2M in NMP) under nitrogen atmosphere over 45 min. The Nα-Fmoc protecting groups were removed by treating the protected peptide resin with a 20% solution of piperidine in DMF, (1×5 min, 1×10 min). The peptide resin was washed three times with DMF and conditioned by shaking with $CH_2Cl_2$ (3×10 min), under nitrogen atmosphere. Benzoyl chloride (178 mL, 1.53 mmol) and $NEt_3$ (428 mL, 3.07 mmol) were added sequentially to a suspension of the amino acid resin above in $CH_2Cl_2$ (10 mL). The mixture was shaken for 2 h under nitrogen atmosphere. The peptide resin was washed with DCM (3×), and the peptide was released from the resin with TFA/DCM (1:1, 10 mL) over 0.5 h. The resin was removed by filtration and the crude peptide was recovered by precipitation with cold anhydrous ethyl ether and purified by semi-preparative RP-HPLC using a gradient of $CH_3CN$ in 0.5% aqueous TFA (from 5 to 95% in 30 min) at a flow rate of 15.0 mL/min. The desired product (RO6039-637) was obtained as the TFA salt as a white solid (6.7 mg, 19%). $^1$H NMR (300 MHz, DMSO-$d_6$) d ppm 0.95-1.51 (m, 6H) 1.64 (d, J=9.80 Hz, 2H) 1.77 (d, J=11.30 Hz, 2H) 2.03-2.22 (m, 1H) 3.02-3.31 (m, 2H) 3.53-3.88 (m, 3H) 5.31-5.46 (m, 1H) 6.71 (br. s., 1H) 7.01 (d, J=7.91 Hz, 1H) 7.16-7.45 (m, 4H) 7.46-7.71 (m, 4H) 7.89-7.99 (m, 1H) 8.46 (dt, J=14.03, 5.42 Hz, 1H); ESI MS m/z: Calculated for $C_{25}H_{29}N_3O_5$ 451.52, Found 452.4 (M+H)+; HPLC (Synergy Hydro, 20 min) $t_R$=16.64 min (90%).

Synthesis of RO6039-639

2-tert-Butoxy-2-oxoethyl N-(phenylcarbonyl)-L-phenylalaninate. N-Benzoyl-L-phenylalanine (500 mg, 1.86 mmol) was placed in ethyl acetate (20 mL), triethylamine (197 mg, 1.95 mmol) added, and the mixture stirred for 10 minutes. tert-Butyl bromoacetate (234 mg, 1.20 mmol) was added and the mixture stirred for 42 hours. At the end of this time, the solid was removed by filtration and washed with ether (50 mL). The filtrates were combined, washed with saturated sodium chloride, and the solvent removed under reduced pressure. The residue was vacuum dried to give 2-tert-butoxy-2-oxoethyl N-(phenylcarbonyl)-L-phenylalaninate as a white solid (386 mg, 83.9%). $^1$H NMR (300 MHz, CHLOROFORM-d) d ppm 1.49 (s, 9H) 3.28 (d, J=6.22 Hz, 1H) 3.39 (d, J=5.65 Hz, 1H) 4.46-4.73 (m, 2H) 5.17 (d, J=7.72 Hz, 1H) 6.43-6.60 (m, 1H) 7.16-7.35 (m, 5H) 7.35-7.56 (m, 3H) 7.63-7.74 (m, 2H).

{[N-(Phenylcarbonyl)-L-phenylalanyl]oxy}acetic acid. 2-tert-Butoxy-2-oxoethyl N-(phenylcarbonyl)-L-phenylalaninate (330 mg, 0.861 mmol) was placed in dry dichloromethane (16 mL), TFA (4 mL) added and the mixture stirred at room temperature for 2.5 hours. At the end of this time, the solvent was evaporated and the residue chased with dichloromethane 3 times. The resulting solid was vacuum dried to give {[N-(phenylcarbonyl)-L-phenylalanyl]oxy}acetic acid as a colorless resin (245 mg, 86.9%). $^1$H NMR (300 MHz, CHLOROFORM-d) d ppm 3.13-3.48 (m, 2H) 4.59-4.87 (m, 2H) 5.17 (q, J=6.72 Hz, 1H) 6.90 (d, J=7.72 Hz, 1H) 7.13-7.32 (m, 4H) 7.32-7.42 (m, 2H) 7.43-7.54 (m, 1H) 7.62 (d, J=7.35 Hz, 2H) 10.58 (br. s., 2H).

[(2-carbamoylcyclohexyl)carbamoyl]methyl-(2S)-3-phenyl-2-(phenylformamido)propanoate (R06039-639)

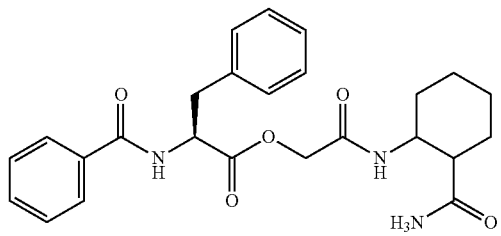 [SMILES: NC(=O)C1CCCCC1NC(=O)COC(=O)[C@H](Cc1ccccc1)NC(=O)c1ccccc1]

Fmoc-trans-(1R/S,2R/S)-2-aminocyclocyclohexanecarboxylic acid was initially coupled to Rink resin (0.52 meq/g), via peptide coupling, using an AAPPTEC Focus peptide synthesizer. The resulting Rink resin (130 mg, 0.0767 mmol) was washed with DMF (5×10 mL) and the Nα-Fmoc protecting group was removed with a 20% solution of piperidine in DMF (1×5 min, 1×10 min), followed by a DMF wash (3×). The resin was then coupled with {[N-(phenylcarbonyl)-L-phenylalanyl]oxy}acetic acid (200 mg, 0.611 mmol) using HBTU and HOBt (1.5 mL, 0.5M each in DMF), in the presence of DIEA (0.8 mL, 2M in NMP), over 45 min. The peptide resin was then washed with dichloromethane (3×) and methanol (3×), and the peptide was released from the resin by stirring with a mixture of TFA/dichloromethane (1:2, 18 mL) for 1.5 hours. The resin mixture was filtered and the solvent removed from the filtrate under vacuum. The filtrate residue was chased several times with dichloromethane and then purified by preparative thin layer chromatography (silica, 20×20 cm plate, 1000 microns, 98% ETOAC/2% methanol) to give R06039-639 as the TFA salt (12.3 mg; 28.3%). $^1$H NMR (300 MHz, METHANOL-4) d ppm 1.11-1.45 (m, 5H) 1.55 (d, J=12.62 Hz, 1H) 1.76 (d, J=10.55 Hz, 2H) 1.90 (br. s., 2H) 2.41 (d, J=10.93 Hz, 1H) 3.12-3.43 (m, 2H) 3.96 (br. s., 1H) 4.31-4.48 (m, 1H) 4.54-4.83 (m, 2H) 7.11-7.36 (m, 5H) 7.38-7.61 (m, 3H) 7.66-7.88 (m, 2H). ESI MS m/z: Calculated for $C_{25}H_{29}N_5O_3$ 451.51, Found 452.5 (M+H)$^+$.

Synthesis of R06039-641

Benzyl (S)-2-(benzyloxy)-3-phenylpropanoate (15) L-(−)-3-Phenylacetic acid (14) (1 g, 6.02 mmol) was dissolved in 20 mL of dry acetonitrile. To it was added Ag$_2$O (5.6 g, 24.07 mmol), molecular sieves 4 Å (0.5 g) followed by slow addition of benzyl bromide (2.8 mL, 24.07 mmol) at room temperature. This mixture was stirred at 60° C. for 16 h. Solids were filtered and the filtrate was concentrated to give crude mixture. The crude product was purified by silica flash chromatography (EtOAc:hexanes) to provide benzyl (S)-2-(benzyloxy)-3-phenylpropanoate as colorless liquid (1.3 g, 65%). H NMR (CDCl$_3$, 300 MHz) δ 3.05-3.08 (m, 2H), 4.17 (t, J=6.00 Hz, 1H), 4.36 (d, J=12.00 Hz, 1H), 4.63 (d, J=12.00 Hz, 1H), 5.14 (s, 2H), 7.12-7.44 (m, 15H). MS m/z: Calcd. for $C_{23}H_{22}O_3$ 346.42 [M]$^+$, found 369.4 [M+Na]$^+$.

(S)-2-(Benzyloxy)-3-phenylpropanoic acid (16) Benzyl (S)-2-(benzyloxy)-3-phenylpropanoate (15) (0.400 g, 1.15 mmol) was mixed with 6N HCl and 1,4-dioxane (3 mL). This mixture was stirred at 60° C. for 24 h. The reaction mixture was diluted with water and the product was extracted in CH$_2$Cl$_2$. Subsequently, the organic layer was separated, dried with Na$_2$SO$_4$, filtered and concentrated in vacuo. The crude product was purified by silica flash chromatography (EtOAc:hexanes) to provide (S)-2-(benzyloxy)-3-phenylpropanoic acid as colorless foam (0.17 g, 87%). NMR (CDCl$_3$, 500 MHz) δ 3.02-3.23 (m, 2H), 4.22 (t, J=6.00 Hz, 1H), 4.44 (d, J=12.00 Hz, 1H), 4.63 (d, J=12.00 Hz, 1H), 7.15-7.65 (m, 8H), 8.12 (d, J=9.00 Hz, 2H). MS m/z: Calcd. for $C_{16}H_{16}O_3$ 256.30 [M]$^+$, found 255.6 [M−1]$^+$.

Trans-2-(2-((S)-2-(benzyloxy)-3-phenylpropanamido)acetamido)cyclohexanecarboxamide (R06039-641)

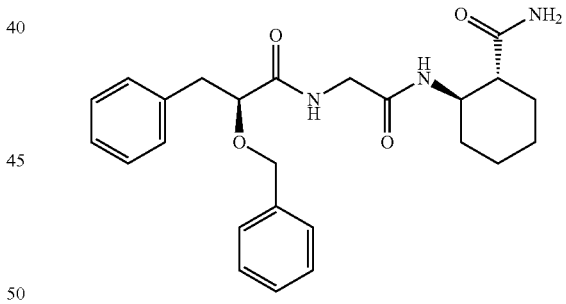

The title compound R06039-641 was obtained using (S)-2-(benzyloxy)-3-phenylpropanoic acid (16) and following the procedure as described in Scheme 1. (8 mg, 69%); White solid. $^1$H NMR (MeOH-d$_4$, 300 MHz) S 1.21-1.62 (m, 5H), 1.78 (d, J=10.93 Hz, 2H), 1.89-1.99 (m, 2H), 2.27 (t, J=11.11 Hz, 1H), 2.93 (ddd, J=14.03, 8.57, 3.01 Hz, 1H), 3.07-3.13 (m, 2H), 3.65-3.85 (m, 1H), 3.86-4.01 (m, 2H), 4.07 (dd, J=8.29, 3.77 Hz, 1H), 4.39 (dd, J=11.87, 3.96 Hz, 1H), 4.63 (dd, J=11.68, 7.16 Hz, 1H), 7.07-7.38 (m, 10H), 7.77 (bs, 1H), 8.09 (br. s., 1H). MS m/z: Calcd. for $C_{25}H_{31}N_3O_4$ 437.53 [M]+, found 438.4 [M+H]+.

Synthesis of R06039-642 tert-Butyl {3-[(2S)-2-carbamoylpiperidin-1-yl]propyl}carbamate. Piperidine-2-carboxamide (108 mg, 0.843 mmol) and tert-butyl N-(3-bromopropyl)carbamate (200 mg, 0.840 mmol) were dissolved in DMF. Potassium carbonate (350 mg, 2.53 mmol) was added and the mixture stirred at room temperature overnight, followed by 1.5 hours at 50° C. The mixture was cooled to room temperature and the solvent removed under reduced pressure. The residue was purified by preparative thin layer chromatography (silica, 20×20 cm plate, 1000 microns, 50% CMA 80/50% dichloromethane), to give tert-butyl {3-[(2S)-2-carbamoylpiperidin-1-yl]propyl}carbamate as a white film (75 mg, 31.3%). $^1$H NMR (300 MHz, CHLOROFORM-d) d ppm 1.27 (d, J=12.06 Hz, 1 H) 1.38-1.82 (m, 14H) 1.82-2.05 (m, 3H) 2.17 (s, 1H) 2.66 (dd, J=10.64, 3.49 Hz, 2H) 3.01-3.32 (m, 3H) 4.54-5.11 (m, 1H) 5.33-5.79 (m, 1H) 6.37-6.94 (m, 1H). ESI MS m/z: Calculated for $C_{14}H_{27}N_3O_3$ 285.38, Found 286.6 (M+H)$^+$.

(2S)-1-(3-Aminopropyl)piperidine-2-carboxamide. tert-Butyl {3-[(2S)-2-carbamoylpiperidin-1-yl]propyl}carbamate (150 mg, 0.526 mmol) was dissolved in 6M HCl and stirred for 1.25 hours. At the end of this time, the solvent was removed with a slow stream of nitrogen. THF (5 mL) was added to the residue and evaporated under vacuum, overnight, at room temperature. The resulting product, (2S)-1-(3-aminopropyl)piperidine-2-carboxamide (0.526 mmol) was used below without further purification. ESI MS m/z: Calculated for $C_9H_{19}N_3O$ 185.27, Found 186.1 (M+H)$^+$.

(2S)-1-{3-[(2S)-3-phenyl-2-(phenylformamido)propanamido]propyl}piperidine-2-carboxamide (R06039-642)

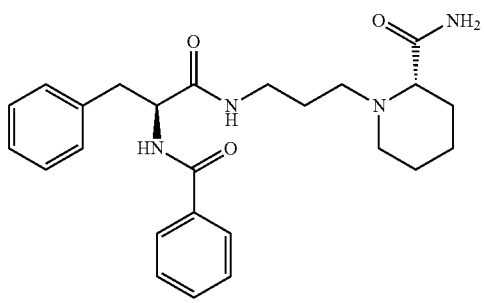 [SMILES: NC(=O)[C@@H]1CCCCN1CCCNC(=O)[C@H](Cc1ccccc1)NC(=O)c1ccccc1]

N-(Phenylcarbonyl)-L-phenylalanine (177 mg, 0.657 mmol), HBTU (249 mg, 0.657 mmol), HOBT (89 mg, 0.659 mmol) and DIEA (750 mg, 5.80 mmol) were dissolved in DMF (2 mL) and stirred at room temperature for 30 minutes. A solution of (2S)-1-(3-aminopropyl)piperidine-2-carboxamide (0.526 mmol) in DMF (4 mL) was added and the mixture stirred at room temperature overnight, under nitrogen. Ethyl acetate was added and the solution was washed with water, saturated sodium bicarbonate solution, and saturated sodium chloride solution. The organic layer was dried over sodium sulfate and the solvent removed under reduced pressure. The residue was initially purified by preparative thin layer chromatography (silica, 20×20 cm plate, 1000 microns, 40% CMA 80/60% dichloromethane). Subsequent purification by semi-preparative RP-HPLC (gradient of CH$_3$CN in 0.5% aqueous TFA, 5%, to 50% in 30 min to 95% in 10 min, with a hold at 50% for 5 min, flow rate 15 mL/min) afforded R06039-642 as a white solid (19.7 mg; 8.6%)$^1$H NMR (300 MHz, DMSO-do) d ppm 1.43 (d, J=9.61 Hz, 1H) 1.53-1.92 (m, 6H) 2.06 (d, J=13.19 Hz, 1H) 2.77-3.29 (m, 7H) 3.43 (d, J=11.49 Hz, 1H) 3.63-3.82 (m, 1H) 4.53-4.69 (m, 1H) 7.08-7.21 (m, 1H) 7.22-7.58 (m, 7H) 7.70-7.87 (m, 3H) 8.05-8.37 (m, 2H) 8.63 (d, J=8.29 Hz, 1H). ESI MS m/z: Calculated for $C_{25}H_{32}N_4O_3$ 436.55, Found 437.5 (M+H)$^+$.

Synthesis of R06039-644, Scheme 1

Methyl 2-(hydroxy(phenyl)methyl)acrylate (2) Benzaldehyde (1) (3.0 g, 28.27 mmol), methyl acrylate (14.15 g, 141.35 mmol) and DABCO (3.17 g, 28.27 mmol) was mixed with MeOH (15 mL). The mixture was stirred at 0° C. for 48 h. Methanol was evaporated in vacuo. The residue was diluted with EtOAc and washed with 0.1 N HCl (2×100 mL) and sat. aqueous NaHCO$_3$ solution. The organic layer was separated, dried with Na$_2$SO$_4$, filtered and concentrated in vacuo. The crude product was purified by silica flash chromatography (EtOAc:hexanes) to provide Methyl 2-(hydroxy(phenyl)methyl)acrylate as colorless liquid (4.7 g, 87%). $^1$H NMR (CDCl$_3$, 300 MHz) δ 3.05 (dd, J=5.65, 1.32 Hz, 1H), 3.72 (s, 3H), 5.56 (d, J=5.46 Hz, 1H), 5.83 (t, J=1.22 Hz, 1H), 6.31-6.37 (m, 1H), 7.12-7.50 (m, 5H). MS m/z: Calcd. for $C_{11}H_{12}O_3$ 192.21 [M]$^+$, found 215.1 [M+Na]$^+$.

Methyl 2-(acetoxy(phenyl)methyl)acrylate (3) To a mixture of methyl 2-(hydroxy(phenyl)methyl)acrylate (2) (0.5 g, 2.60 mmol) in dry CH$_2$Cl$_2$ was added pyridine (0.27 mL, 3.38 mmol) followed by dropwise addition of acetyl chloride (0.24 mL, 3.38 mmol) at 0° C. The mixture was stirred at 0° C. for 1.5 h. The reaction mixture was diluted with CH$_2$Cl$_2$ and washed with 1 N HCl (50 mL). The organic layer was separated, washed with brine, dried with Na$_2$SO$_4$, filtered and concentrated in vacuo. The crude product was purified by silica flash chromatography (EtOAc:hexanes) to provide the title product as colorless liquid (0.56 g, 92%), $^1$H NMR (CDCl$_3$, 300 MHz) δ 2.11 (s, 3H), 3.72 (s, 3H), 5.87 (s, 1H), 6.40 (s, 1H), 6.68 (s, 1H), 7.25-7.30 (m, 1H), 7.21-7.52 (m, 5H). Calcd. for $C_{13}H_{14}O_4$ 234.25 [M]$^+$, found 235.3 [M+H]$^+$.

Methyl (E)-2-benzylidene-4-phenylbutanoate (4) To a stirred solution of methyl 2-(acetoxy(phenyl)methyl)acrylate (3) (1.6 g, 6.78 mol) in anhydrous diethyl ether (25 mL) was slowly added benzyl magnesium bromide (1 M in ether) (8.14 mL, 8.16 mmol) with cooling to −40° C. The resulting solution was stirred at −40° C. for 1 h. The solution was slowly warmed to −5° C. and stirred at this temperature for 2 h. The solution was subsequently quenched with sat. aq. NH$_4$Cl (25 mL) and water (100 mL) was added. The aqueous layer was extracted in EtOAc (3×100 mL). The combined organic layer was then washed with brine (50 mL), dried with Na$_2$SO$_4$ and the solvent was removed in vacuo. Crude product was purified by silica gel flash chromatography (EtOAc/hexanes) to provide methyl (E)-2-benzylidene-4-phenylbutanoate as colorless oil (1.4 g, 77%). $^1$H NMR (CDCl$_3$, 300 MHz) δ 2.81-2.88 (m, 4H), 3.83 (s, 3H), 7.13-7.24 (m, 3H), 7.26-7.42 (m, 7H), 7.72 (s, 1H). Calcd. for $C_{18}H_{18}O_2$ 266.33 [M]$^+$, found 267.2 [M+H]$^+$.

Methyl 2-benzyl-4-phenylbutanoate (5) A mixture of methyl (E)-2-benzylidene-4-phenylbutanoate (4) (0.800 g, 3.00 mol) and 10% Pd/C (260 g) in MeOH (40 mL) was hydrogenated at 45 psi for 4 h. The mixture was filtered through celite pad and concentrated to obtain crude methyl 2-benzyl-4-phenylbutanoate as colorless oil (0.76 g, 94%). $^1$H NMR (CDCl$_3$, 300 MHz) δ 1.75-1.86 (m, 1H), 1.92-2.08 (m, 1H), 2.49-2.84 (m, 4H), 2.89-3.06 (m, 1H), 3.61 (s, 3H), 7.10-7.16 (m, 4H), 7.17-7.23 (m, 2H), 7.23-7.31 (m, 4H). Calcd. for $C_{18}H_{20}O_2$ 268.35 [M]$^+$, found 269.2 [M+H]$^+$.

2-Benzyl-4-phenylbutanoic acid (6) Lithium hydroxide monohydrate (0.260 g, 6.15 mmol) in 3.0 mL of water was added to a solution of methyl 2-benzyl-4-phenylbutanoate (5) (0.550 g, 2.05 mmol) in MeOH (8 mL) and THF (2 mL). The reaction mixture was stirred at RT for 4 h and then concentrated to about half the volume. Residue was diluted with water (pH 9) and then extracted with ether (2×30 mL). The aqueous layer was acidified using 1 N HCl to pH 2 and extracted with $CH_2Cl_2$ (3×50 mL). The combined organic layers were washed with water, brine and then dried with $Na_2SO_4$. The solvent was evaporated in vacuo to provide 2-benzyl-4-phenylbutanoic acid as oil (0.380 g, 73%). $^1H$ NMR ($CDCl_3$, 300 MHz) δ 1.74-1.91 (m, 1H), 1.92-2.10 (m, 1H), 2.53-2.88 (m, 4H), 2.94-3.11 (m, 1H), 6.98-7.38 (m, 10H). Calcd. for $C_{17}H_{18}O_2$ 254.32 $[M]^+$, found 253.3 $[M-H]^+$.

Tert-butyl (2-benzyl-4-phenylbutanoyl)glycinate (7) 2-Benzyl-4-phenylbutanoic acid (6) (100 mg, 0.39 mmol) was dissolved in THF (6 mL). To the solution was added BOP (191 mg, 0.43 mmol) and triethylamine (0.16 mL, 1.18 mmol). The resulting mixture was stirred at room temperature for 15 minutes. Glycine tert-butyl ester hydrochloride (72 mg, 0.43 mmol) was added and stirred at room temperature for 3 h. THF was evaporated in vacuo, water was added to the residue and the aqueous layer was extracted with $CH_2Cl_2$ (3×25 mL). The combined organic layer was washed with water, brine and then dried with $Na_2SO_4$. The solvent was evaporated in vacuo to give the crude residue. The residue was purified by silica gel flash chromatography (EtOAc:Hex) to provide tert-butyl (2-benzyl-4-phenylbutanoyl)glycinate as a white solid (0.11 mg, 76%). $^1H$ NMR ($CDCl_3$, 300 MHz) δ 1.45 (s, 9H), 1.72-1.87 (m, 1H), 1.99-2.13 (m, 1H), 2.31-2.41 (m, 1H), 2.50-2.62 (m, 1H), 2.66-2.78 (m, 2H), 2.91-2.99 (m, 1H), 3.71 (dd, J=18.46, 4.52 Hz, 1H), 3.96 (dd, J=18.37, 5.37 Hz, 1H), 5.65 (br. s., 1H), 7.08-7.26 (m, 9H), 7.29 (s, 1H). Calcd. for $C_{23}H_{29}NO_3$ 367.48 $[M]^+$, found 368.4 $[M+H]^+$.

Ethyl trans-2-(2-(2-benzyl-4-phenylbutanamido) acetamido)cyclohexane-1-carboxylate (8)

Trifluoroacetic acid (0.8 mL) was added dropwise to a solution of tert-butyl (2-benzyl-4-phenylbutanoyl)glycinate (7) (100 mg, 0.27 mmol) in $CH_2Cl_2$ (2.0 mL). The reaction mixture was stirred at room temperature for 4 h and then the solvent was evaporated in vacuo and dried to give (2-benzyl-4-phenylbutanoyl)glycine as colorless foam that was used without further purification (90 mg, 85%).

(2-Benzyl-4-phenylbutanoyl)glycine (50 mg, 0.16 mmol) was dissolved in DCM (8 mL). To the solution was added EDC.HCl (40 mg, 0.20 mmol), triethylamine (0.22 mL, 1.60 mmol) and ethyl trans-2-amino-1-cyclohexane (33 mg, 0.16 mmol). The resulting mixture was stirred at room temperature for 16 h. Reaction mixture was diluted with $CH_2Cl_2$ and washed with water and brine. The organic layer was separated, dried with $Na_2SO_4$ and filtered. The filterate was evaporated in vacuo to give the crude residue which was purified by silica gel flash chromatography (EtOAc:Hex) to give ethyl trans-2-(2-(2-benzyl-4-phenylbutanamido)acetamido)cyclohexane-1-carboxylate as a colorless foam (45 mg, 60%). $^1H$ NMR ($CDCl_3$, 300 MHz) δ 1.20 (t, J=6.0 Hz, 3H) 1.09-1.28 (m, 3H), 1.67-1.83 (d, J=11.49 Hz, 3H), 1.88-2.11 (m, 3H), 2.32-2.45 (m, 1H), 2.49-2.82 (m, 3H), 2.87-2.99 (m, 1H), 3.58-3.87 (m, 3H), 3.95 (d, J=7.72 Hz, 1H), 4.00-4.17 (m, 2H), 5.76 (br. s., 1H), 5.90 (br. s., 1H), 7.05-7.22 (m, 6H), 7.22-7.32 (m, 4H). Calcd. for $C_{28}H_{36}N_2O_4$ 464.60 $[M]^+$, found 365.5 $[M+H]^+$.

Trans-2-(2-(2-benzyl-4-phenylbutanamido)acet-amido)cyclohexanecarboxamide (R06039-644)

Lithium hydroxide monohydrate (8.1 mg, 0.19 mmol) in 1.5 mL of water was added to a solution of ethyl trans-2-(2-(2-benzyl-4-phenylbutanamido)acetamido)cyclohexane-1-carboxylate (8) (30 mg, 0.06 mmol) in MeOH (6 mL) and THF (1 mL). The reaction mixture was stirred at room temperature for 16 h and then concentrated to about half the volume. Residue was diluted with water (pH 9) and then extracted with ether (2×25 mL). The aqueous layer was acidified using 1 N HCl to pH 2 and extracted with $CH_2Cl_2$ (3×50 mL). The combined organic layers were washed with water, brine and then dried with $Na_2SO_4$ and filtered. The solvent was evaporated in vacuo to give trans2-(2-(2-benzyl-4-phenylbutanamido)acetamido)cyclohexanecarboxylic acid as white solid that was used without further purification (23 mg, 28%). Trans2-(2-(2-benzyl-4-phenylbutanamido) acetamido)cyclohexanecarboxylic acid (20 mg, 0.04 mmol) was dissolved in THF (5 mL). To the solution was added BOP (18 mg, 0.04 mmol) and triethylamine (0.040 mL, 0.14 mmol). The resulting mixture was stirred at room temperature for 15 minutes. To the reaction mixture was slowly added 0.5 M $NH_3$ in THF (0.2 mL, 0.14 mmol) and stirred at room temperature for 3 h. THF was evaporated in vacuo, water was added to the residue and the aqueous layer was extracted with $CH_2Cl_2$ (3×25 mL). The combined organic layers were washed with water, brine and then dried with $Na_2SO_4$. The solvent was evaporated in vacuo to give the crude residue. The residue was purified by silica gel flash chromatography (MeOH:$CH_2Cl_2$) to give R06039-644 as white solid (15 mg, 76%). $^1H$ NMR (MeOH-$d_4$, 500 MHz) δ 1.18-1.38 (m, 3H), 1.47-156 (m, 1H), 1.70-1.76 (m, 3H), 1.90-1.98 (m, 3H), 2.18-2.26 (m, 1H), 2.52-2.69 (m, 1H), 2.73 (dd, J=6.50 Hz, J=6.00 Hz, 1H), 2.87-2.93 (m, 1H), 3.44-3.54 (m, 2H), 3.65-3.74 (m, 2H), 3.81-3.91 (m, 1H), 7.12-7.18 (m, 6H), 7.21-7.26 (m, 4H). MS m/z: Calcd. for $C_{26}H_{33}N_3O_3$ 435.56 $[M]^+$, found 436.8 $[M+H]^+$.

(1R/S,2S/R)-2-(2-cinnamamidoacetamido)cyclo-hexanecarboxamide (R06039-655)

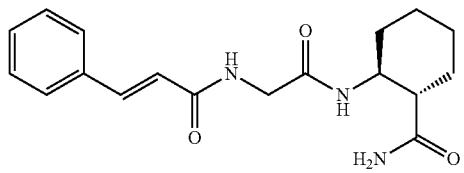 [SMILES: NC(=O)[C@H]1CCCC[C@@H]1NC(=O)CNC(=O)/C=C/c1ccccc1]

Fmoc-trans-(1R/S,2R/S)-2-aminocyclocyclohexanecarboxylic acid was coupled to Rink resin (0.52 meq/g) via peptide coupling using an AAPPTEC Focus peptide synthesizer. Rink resin (130 mg) was washed with DMF (5×10 mL) and the Nα-Fmoc protecting group removed with a 20% solution of piperidine in DMF (1×5 min, 1×10 min) followed by DMF wash (3×). Nα-Fmoc-Gly-OH was added in a 3-fold excess and coupled with HBTU and HOBt (1.5 mL, 0.5M each in DMF) in the presence of DIEA (0.8 mL, 2M in NMP) under nitrogen atmosphere over 45 min. The Nα-Fmoc protecting group was removed by treating the protected peptide resin with a 20% solution of piperidine in DMF, (1×5 min, 1×10 min). The peptide resin was washed three times with DMF and conditioned by shaking with CH$_2$Cl$_2$ (3×10 min), under nitrogen atmosphere. The peptide resin was washed three times with DMF and then coupled with trans-cinnamic acid (3 equivalents) with HBTU and HOBt (1.5 mL, 0.5M each in DMF) in the presence of DIEA (0.8 mL, 2M in NMP) under nitrogen atmosphere over 45 min. The peptide resin was washed with DMF (3× and DCM (3×), and the peptide was released from the resin with TFA/DCM (1:1, 10 mL) over 0.5 h. The resin was removed by filtration and the crude peptide was recovered by precipitation with cold anhydrous ethyl ether and purified by semi-preparative RP-HPLC using a gradient of CH$_3$CN in 0.5% aqueous TFA (from 5 to 95% in 30 min) at a flow rate of 15.0 mL/min. The desired product R06039-655 was obtained as a white solid (14.4 mg, 56%). $^1$H NMR (300 MHz, DMSO-d$_6$) d ppm 1.03-1.48 (m, 4H) 1.58-1.87 (m, 4H) 2.14 (td, J=11.40, 3.58 Hz, 1H) 3.64-3.87 (m, 3H) 6.05-6.05 (m, 0H) 6.66-6.76 (m, 2H) 6.79 (s, 1H) 6.99 (s, 1H) 7.33-7.47 (m, 4H) 7.57 (dd, J=7.91, 1.51 Hz, 2H) 7.70 (d, J=8.67 Hz, 1H) 8.26 (t, J=5.65 Hz, 1H); ESI MS m/z: Calculated for C$_{18}$H$_{23}$N$_3$O$_3$ 329.40, Found 352.2 (M+Na)$^+$, 330.3 (M+H)$^+$; HPLC (Synergy Hydro, 20 min) t$_R$=13.33 min (>99.9%).

(1R/S,2S/R)-2-(2-(2-benzyl-3-phenylpropanamido)acetamido)cyclohexanecarboxamide (R06039-656)

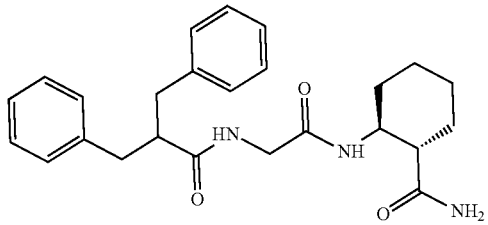 [SMILES: NC(=O)[C@H]1CCCC[C@@H]1NC(=O)CNC(=O)C(Cc1ccccc1)Cc1ccccc1]

Fmoc-trans-(1R/S,2R/S)-2-aminocyclocyclohexanecarboxylic acid was coupled to Rink resin (0.52 meq/g) via peptide coupling using an AAPPTEC Focus peptide synthesizer. Rink resin (130 mg) was washed with DMF (5×10 mL) and the Nα-Fmoc protecting group removed with a 20% solution of piperidine in DMF (1×5 min, 1×10 min) followed by DMF wash (3×). Nα-Fmoc-Gly-OH was added in a 3-fold excess and coupled with HBTU and HOBt (1.5 mL, 0.5M each in DMF) in the presence of DIEA (0.8 mL, 2M in NMP) under nitrogen atmosphere over 45 min. The Nα-Fmoc protecting group was removed by treating the protected peptide resin with a 20% solution of piperidine in DMF, (1×5 min, 1×10 min). The peptide resin was washed three times with DMF and conditioned by shaking with CH$_2$Cl$_2$ (3×10 min), under nitrogen atmosphere. The peptide resin was washed three times with DMF and then coupled with dibenzylacetic acid (3 equivalents) with HBTU and HOBt (1.5 mL, 0.5M each in DMF) in the presence of DIEA (0.8 mL, 2M in NMP) under nitrogen atmosphere over 45 min. The peptide resin was washed with DMF (3× and DCM (3×), and the peptide was released from the resin with TFA/DCM (1:1, 10 mL) over 0.5 h. The resin was removed by filtration and the crude peptide was recovered by precipitation with cold anhydrous ethyl ether and purified by semi-preparative RP-HPLC using a gradient of CH$_3$CN in 0.5% aqueous TFA (from 5 to 95% in 30 min) at a flow rate of 15.0 mL/min. The desired product R06039-656 was obtained as a white solid (12.5 mg, 39%). $^1$H NMR (300 MHz, DMSO-d$_6$) d ppm 0.93-1.46 (m, 6H) 1.55-1.81 (m, 3H) 2.07 (dd, J=11.02, 7.82 Hz, 1H) 2.78-2.98 (m, 3H) 3.43 (dd, J=16.11, 5.37 Hz, 2H) 3.51-3.76 (m, 3H) 6.69 (br. s., 1H) 6.97 (br. s., 1H) 7.10-7.30 (m, 10H) 7.40 (d, J=8.29 Hz, 1H) 8.02 (t, J=5.46 Hz, 1H); ESI MS m/z: Calculated for C$_{25}$H$_{31}$N$_3$O$_3$ 421.45, Found 422.3 (M+H)$^+$; HPLC (Synergy Hydro, 20 min) t$_R$=15.59 min (>99.9%).

(1R/S,2S/R)-2-(2-(2,3-diphenylpropanamido)acetamido)cyclohexanecarboxamide (R06039-657)

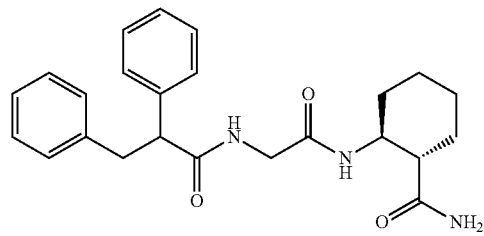 [SMILES: NC(=O)[C@H]1CCCC[C@@H]1NC(=O)CNC(=O)C(Cc1ccccc1)c1ccccc1]

Fmoc-trans-(1R/S,2R/S)-2-aminocyclocyclohexanecarboxylic acid was coupled to Rink resin (0.52 meq/g) via peptide coupling using an AAPPTEC Focus peptide synthesizer. Rink resin (130 mg) was washed with DMF (5×10 mL) and the Nα-Fmoc protecting group removed with a 20% solution of piperidine in DMF (1×5 min, 1×10 min) followed by DMF wash (3×). Nα-Fmoc-Gly-OH was added in a 3-fold excess and coupled with HBTU and HOBt (1.5 mL, 0.5M each in DMF) in the presence of DIEA (0.8 mL, 2M in NMP) under nitrogen atmosphere over 45 min. The Nα-Fmoc protecting group was removed by treating the protected peptide resin with a 20% solution of piperidine in DMF, (1×5 min, 1×10 min). The peptide resin was washed three times with DMF and conditioned by shaking with CH$_2$Cl$_2$ (3×10 min), under nitrogen atmosphere. The peptide resin was washed three times with DMF and then coupled with benzylphenylacetic acid (3 equivalents) with HBTU and HOBt (1.5 mL, 0.5M each in DMF) in the presence of DIEA (0.8 mL, 2M in NMP) under nitrogen atmosphere over 45 min. The peptide resin was washed with DMF (3× and DCM (3×), and the peptide was released from the resin with TFA/DCM (1:1, 10 mL) over 0.5 h. The resin was removed by filtration and the crude peptide was recovered by precipitation with cold anhydrous ethyl ether and purified by semi-preparative RP-HPLC using a gradient of CH$_3$CN in 0.5% aqueous TFA (from 5 to 95% in 30 min) at a flow rate of 15.0 mL/min. The desired product R06039-657 was obtained as a white solid (10 mg, 32%). $^1$H NMR (300 MHz, DMSO-d$_6$) d ppm 1.24 (br. s., 6H) 1.51-1.82 (m, 3H) 2.04 (br. s., 1H) 2.93 (d, J=7.35 Hz, 2H) 3.40-3.75 (m, 3H) 3.94 (s, 1H) 6.68 (br. s., 1H) 6.96 (br. s., 1H) 7.06-7.47 (m, 10H) 8.19 (d, J=5.09 Hz, 1H); ESI MS m/z: Calculated for C$_{24}$H$_{29}$N$_3$O$_3$ 407.51, Found 408.6 (M+H)+; HPLC (Synergy Hydro, 20 min) t$_R$=15.96 min (90%).

3-{N-Benzyl-2-[(2S)-3-phenyl-2-(phenylformamido)propanamido]acetamido}butanamide (R06039-658)

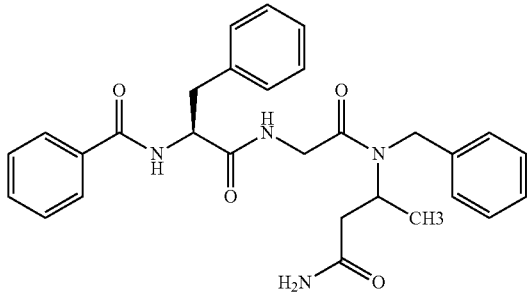 [SMILES: CC(CC(N)=O)N(Cc1ccccc1)C(=O)CNC(=O)[C@H](Cc1ccccc1)NC(=O)c1ccccc1]

N-(phenylcarbonyl)-L-phenylalanylglycine[1] (156 mg; 0.478 mmol) was dissolved in THF (5 mL). BOP (317 mg, 0.717 mmol) and triethylamine (242 mg, 2.39 mmol) were added and the mixture was stirred for 10 minutes. 3-(benzylamino)butanamide[2] (110 mg, 0.572=lop was subsequently added and the solution stirred at room temperature overnight, under nitrogen. Water was added and the mixture extracted with dichloromethane. The organic layer was dried over sodium sulfate and the solvent removed under reduced pressure. The residue was purified twice by preparative thin layer chromatography (silica, 20×20 cm plate, 1000 microns, 1st plate 30% CMA 80/70% dichloromethane, 2nd plate 35% CMA 80/65% dichloromethane) to give R06039-658 as a white solid (36 mg; 15.1%). NMR (300 MHz, DMSO-$d_6$) d ppm 1.06 (d, J=6.40 Hz, 3H) 2.16-2.47 (m, 2H) 2.89-3.08 (m, 1H) 3.10-3.26 (m, 1H) 3.89 (br. s., 1H) 4.17-4.68 (m, 4H) 4.78 (d, J=8.10 Hz, 1H) 6.71-6.98 (m, 1H) 7.07-7.57 (m, 14H) 7.78 (d, J=7.16 Hz, 2H) 8.06-8.25 (m, 1H) 8.51-8.77 (m, 1H). ESI MS m/z: Calculated for $C_{29}H_{32}N_4O_4$ 500.59, Found 501.7 (M+H)$^+$. ([1]-Sandhu, S. S.; Singh, J.; Sharma, S. J. Indian Chem. Soc. 1989, 66(2), 104; [2]-Zilkha, A; Rivlin, J. *J. Org. Chem.* 1958, 23, 95.)

N—((S)-1-(2-(((1R/S,2S/R)-2-carbamoylcyclohexyl)(methyl)amino)-2-oxoethylamino)-1-oxo-3-phenyl-propan-2-yl)benzamide (R06039-662)

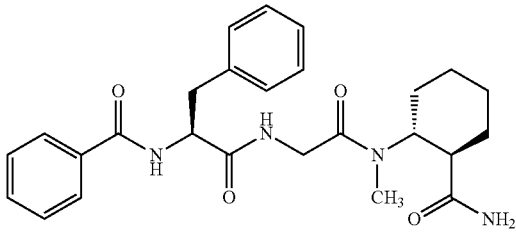 [SMILES: CN(C(=O)CNC(=O)[C@H](Cc1ccccc1)NC(=O)c1ccccc1)[C@@H]1CCCC[C@H]1C(N)=O]

Fmoc-trans-(1R/S,2R/S)-2-aminocyclocyclohexanecarboxylic acid was coupled to Rink resin (0.52 meq/g) via peptide coupling using an AAPPTEC Focus peptide synthesizer. Rink resin (130 mg) was washed with DMF (5×10 mL) and the Nα-Fmoc protecting group removed with a 20% solution of piperidine in DMF, (1×5 min, 1×10 min) followed by DMF wash (3×) and THF wash (3×10 min). The amino acid on resin was suspended in THF (5 mL), and formaldehyde (37% aq, 5 mL) was added. The suspension was shaken for 2 hours, drained, re-filled with formaldehyde (37% aq, 5 mL), shaken for 1 h, drained and filled with THF (1 mL). A mixture of acetic acid/water (1:1, 1 mL) was added and shaken for 5 minutes. A solution of NaCNBH$_3$ (1 N, 1 mL) was added and the suspension shaken for 3 hours. The reaction mixture was drained and washed with water (3×), then DMF (3×). The following protected amino acids were then added stepwise Nα-Fmoc-AA2-OH (AA2: Nα-Fmoc-Gly-OH, Nα-Fmoc-Phe-OH). Each coupling reaction was accomplished using a 3-fold excess of amino acid with HBTU and HOBt (1.5 mL, 0.5M each in DMF) in the presence of DIEA (0.8 mL, 2M in NMP) under nitrogen atmosphere over 45 min. The Nα-Fmoc protecting groups were removed by treating the protected peptide resin with a 20% solution of piperidine in DMF, (1×5 min, 1×10 min). The peptide resin was washed three times with DMF and conditioned by shaking with CH$_2$Cl$_2$ (3×10 min), under nitrogen atmosphere. The peptide resin was washed three times with DMF and then coupled with benzoic acid (3 equivalents) with HBTU and HOBt (1.5 mL, 0.5M each in DMF) in the presence of DMA (0.8 mL, 2M in NMP) under nitrogen atmosphere over 45 min. The peptide resin was washed with DCM (3×), and the peptide was released from the resin with TFA/DCM (1:1, 10 mL) over 0.5 h. The resin was removed by filtration and the crude peptide was recovered by precipitation with cold anhydrous ethyl ether and purified by semi-preparative RP-HPLC using a gradient of CH$_3$CN in 0.5% aqueous TFA (from 5 to 95% in 30 min) at a flow rate of 15.0 mL/min. The desired product R06039-662 was obtained as a white solid (2.1 mg, 6%). $^1$H NMR (300 MHz, DMSO-$d_6$) δ ppm 1.32-1.86 (m, 8H) 2.66-2.77 (m, 3H) 2.90-3.04 (m, 1H) 3.09-3.23 (m, 1H) 3.67 (br. s., 2H) 4.11 (t, J=4.90 Hz, 1H) 4.76 (tt, J=7.68, 4.10 Hz, 1H) 6.81 (br. s., 1H) 7.07-7.29 (m, 3H) 7.32-7.55 (m, 6H) 7.77 (d, J=7.72 Hz, 2H) 7.94-8.09 (m, 1H) 8.66 (d, J=8.85 Hz, 1H); ESI MS m/z: Calculated for $C_{24}H_{29}N_3O_3$ 464.57, Found 465.4 (M+H)+; HPLC (Synergy Hydro, 20 min) to = 15.16 min (>99.9%).

N—((S)-1-(2-((S)-3-amino-3-oxo-1-phenylpropylamino)-2-oxoethylamino)-1-oxo-3-phenylpropan-2-yl)benzamide (R06039-663)

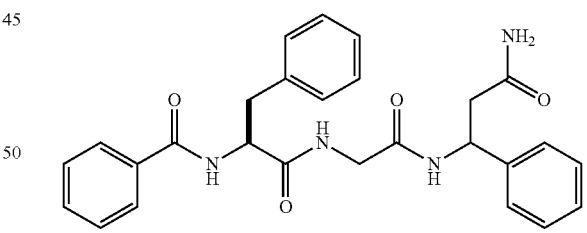

Nβ-Fmoc-(R)-3-amino-3-phenylpropanoic acid (250 mg) was coupled to Rink resin (0.52 meq/g) via peptide coupling using an AAPPTEC Focus peptide synthesizer. Rink resin (130 mg) was washed with DMF (5×10 mL) and the Nα-Fmoc protecting group removed with a 20% solution of piperidine in DMF, (1×5 min, 1×10 min) followed by DMF wash (3×). The following protected amino acids were then added stepwise Nα-Fmoc-AA2-OH (AA2: Nα-Fmoc-Gly-OH, Na-Fmoc-Phe-OH). Each coupling reaction was accomplished using a 3-fold excess of amino acid with HBTU and HOBt (1.5 mL, 0.5M each in DMF) in the presence of DIEA (0.8 mL, 2M in NMP) under nitrogen atmosphere over 45 min. The Nα-Fmoc protecting groups were removed by treating the protected peptide resin with a 20% solution of piperidine in DMF, (1×5 min, 1×10 min). The peptide resin was washed three times with DMF and conditioned by shaking with CH$_2$Cl$_2$ (3×10 min), under nitrogen atmosphere. The peptide resin was washed three times with DMF and then coupled with benzoic acid (3 equivalents) with HBTU and HOBt (1.5 mL, 0.5M each in DMF) in the presence of DIEA (0.8 mL, 2M in NMP) under nitrogen atmosphere over 45 min. The peptide resin was washed with DCM (3×), and the peptide was released from the resin with TFA/DCM (1:1, 10 mL) over 0.5 h. The resin was removed by filtration and the crude peptide was recovered by precipitation with cold anhydrous ethyl ether and dried in vacuo. The desired product R06039-663 was obtained as a white solid (20 mg, 89%). $^1$H NMR (300 MHz, DMSO-d$_6$) d ppm 3.04 (d, J=10.55 Hz, 3H) 3.16 (br. s., 1H) 3.75 (d, J=5.65 Hz, 2H) 4.67 (br. s., 1H) 5.22 (d, J=8.29 Hz, 1H) 6.81 (br. s., 1H) 7.09-7.56 (m, 14H) 7.79 (d, J=6.97 Hz, 2H) 8.29-8.45 (m, 2H) 8.67 (d, J=8.10 Hz, 1H) ESI MS m/z: Calculated for C$_{27}$H$_{28}$N$_4$O$_4$ 472.54, Found 473.3 (M+H)$^+$; HPLC (Synergy Hydro, 20 min) t$_R$=15.63 min (>98%).

Synthesis if R06039-675

(E)-2-Benzylidene-4-phenylbutanoic acid. Lithium hydroxide monohydrate (0.118 g, 2.81 mmol) in 1.5 mL of water was added to a solution of methyl (E)-2-benzylidene-4-phenylbutanoate (4) (0.300 g, 1.12 mmol) in MeOH (10 mL) and THF (1 mL). The reaction-Mixture was stirred at room temperature for 16 h and then concentrated to about half the volume. Residue was diluted with water (pH 9) and then extracted with ether (2×25 mL). The aqueous layer was acidified using 1 N HCl to pH 2 and extracted with CH$_2$Cl$_2$ (3×50 mL). The combined organic layers were washed with water, brine and then dried with Na$_2$SO$_4$. The solvent was evaporated in vacuo to give (E)-2-benzylidene-4-phenylbutanoic acid as white solid (0.27 g, 96%). $^1$H NMR (CDCl$_3$, 300 MHz) δ 2.81-2.96 (m, 4H), 7.16-7.25 (m, 3H), 7.26-7.43 (m, 7H), 7.83-7.93 (m, 1H), 11.51 (br. s., 1H). Calcd. for C$_{17}$H$_{16}$O$_2$ 252.31 [M]$^+$, found 251.4 [M−H]$^+$.

Trans-2-(2-((E)-2-Benzylidene-4-phenylbutanamido)acetamido)cyclohexanecarboxamide (R06039-675)

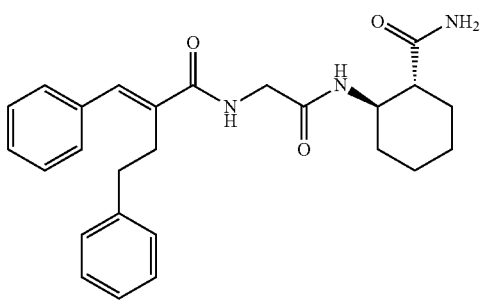 [SMILES: NC(=O)[C@@H]1CCCC[C@H]1NC(=O)CNC(=O)/C(=C/c1ccccc1)CCc1ccccc1]

The title compound was prepared in a manner analogous to that of R06039-644 to afford R06039-675 as a white solid (8 mg, 79%). NMR (CDCl$_3$, 300 MHz) S 1.07-1.54 (m, 5H), 1.70-1.85 (m, 3H), 1.94-2.08 (m, 2H), 2.20-2.36 (m, 1H), 2.77-2.90 (m, 3H), 3.35-4.10 (m, 3H), 5.76 (br. s., 1H) 6.21 (br. s., 1H), 6.80 (d, J=8.29 Hz, 1H), 6.97 (br. s., 1H), 7.09-7.42 (m, 10H). MS m/z: Calcd. for C$_{26}$H$_{31}$N$_3$O$_3$ 433.54 [M]$^+$, found 434.4 [M+H]$^+$.

Trans-2-(2-(2-Benzyl-4-cyclohexylbutanamido)acetamido)cyclohexanecarboxamide (R06039-682)

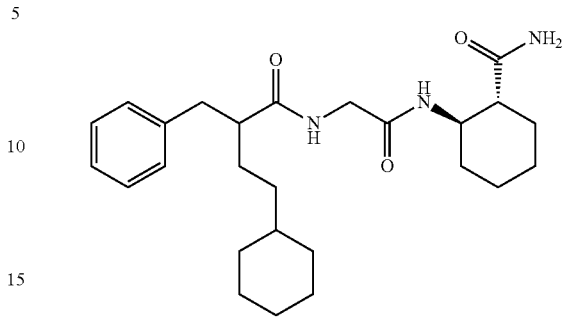

The title compound (R06039-682) was synthesized using the procedure as described in Scheme 1 to afford a white solid (7 mg, 82%). $^1$H NMR (DMSO-d$_6$, 300 MHz) δ 0.68-0.91 (m, 2H), 0.99-1.84 (m, 10H), 1.35-1.53 (m, 2H), 1.54-170 (m, 8H), 1.70-1.84 (m, 2H), 1.94-2.15 (m, 2H), 2.75-2.90 (br. s., 1H), 3.54-3.75 (m, 2H), 6.70 (br. s., 1H), 7.00 (br. s., 1H), 7.11-7.29 (m, 4H), 7.42 (d, J=5.65 Hz, 1H), 7.99 (d, J=6.22 Hz, 1H). MS m/z: Calcd. for C$_{26}$H$_{39}$N$_3$O$_3$ 441.61 [M]$^+$, found 442.7 [M+H]$^+$.

Trans-2-(2-(2-Benzyl-5-methylhexanamido)acetamido)cyclohexanecarboxamide (R06039-686)

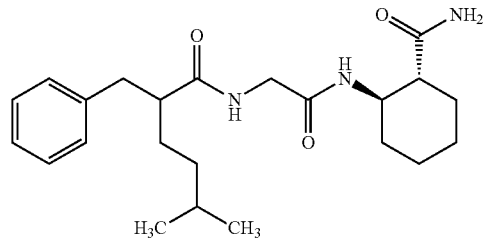 [SMILES: CC(C)CCC(Cc1ccccc1)C(=O)NCC(=O)N[C@@H]1CCCC[C@H]1C(N)=O]

The title compound (R06039-686) was synthesized using the procedure as described in Scheme 1 to afford a white solid (11 mg, 70%). $^1$H NMR (DMSO-d$_6$, 300 MHz) δ 0.78 (t, J=6.69 Hz, 6H), 1.00-1.15 (m, 4H), 1.18-1.31 (m, 3H), 1.34-1.54 (m, 3H), 1.56-1.69 (m, 2H), 1.70-0.84 (m, 2H), 2.09 (br. s., 1H), 2.75-2.87 (br. s., 1H), 3.56 (br. s., 1H), 3.62-3.79 (m, 2H), 6.70 (br. s., 1H), 7.01 (br. s., 1H), 7.11-7.30 (m, 5H), 7.45 (br. s., 1H), 7.98 (br. s., 1H). MS m/z: Calcd. for C$_{23}$H$_{35}$N$_3$O$_3$ 401.54 [M]+, found 402.4 [M+H]+.

Synthesis of R06039-691

3-(Methoxycarbonyl)bicyclo[2.2.2]oct-5-ene-2-carboxylic acid

Bicyclo[2.2.2]octane-2,3-dicarboxylic anhydride (1.0 g, 6.09 mmol) was dissolved in anhydrous tetrahydrofuran (3 mL) and cooled to 0° C. Sodium methoxide solution (0.5M, 16.8 mL, 8.42 mmol) was then added dropwise over 10 minutes. The solution was then stirred at room temperature for 20 hours. A second portion of sodium methoxide (8.4 mL; 4.21 mmol) was added and the mixture refluxed for 7 hours. The solution was allowed to cool to room temperature and stir for an additional 13 hours. The reaction volume was reduced by approximately one half and the mixture poured into cold 2N HCl (50 mL). The resulting solution was extracted several times with chloroform, and the organic layers combined and dried over sodium sulfate. The solvent was removed under reduced pressure and the residue vacuum dried to give 3-(methoxycarbonyl)bicyclo[2.2.2] oct-5-ene-2-carboxylic acid as an off white solid (1.04 g, 88.2%). ¹H NMR (300 MHz, CHLOROFORM-d) d ppm 1.03-1.22 (m, 1H) 1.31 (s, 1H) 1.41-1.58 (m, 1H) 1.59-1.72 (m, 1H) 2.77-3.12 (m, 3H) 3.21 (d, J=2.26 Hz, 1H) 3.73 (s, 3H) 6.22 (s, 1H) 6.33-6.43 (m, 1H).

Methyl 3-{[(benzyloxy)carbonyl]amino}bicyclo[2.2.2]oct-5-ene-2-carboxylate 3-(Methoxycarbonyl)bicyclo[2.2.2]oct-5-ene-2-carboxylic acid (1.03 g, 4.9 mmol) was dissolved in toluene (15 mL). Diphenylphosphoryl azide (1.48 g, 5.38 mmol) and triethylamine (544 mg, 5.38 mmol) were added and the mixture heated at 90° C. for 2.5 hours. Benzyl alcohol (530 mg, 4.9 mmol) was then added and the mixture heated at 90° C. for 2.5 days. The mixture was cooled to room temperature, diluted with ethyl acetate (100 mL), and extracted with saturated sodium bicarbonate solution several times. The organic layer was dried over sodium sulfate and the solvent removed under reduced pressure. The mixture was purified by silica gel chromatography (40% ethylacetate/60% hexane) to give methyl 3-[{(benzyloxy)carbonyl] amino}bicyclo[2.2.2]oct-5-ene-2-carboxylate as a colorless liquid (840 mg, 54.4%). ¹H NMR (300 MHz, CHLOROFORM-d) d ppm 0.97-1.15 (m, 1H) 1.19-1.36 (m, 1H) 1.63 (s, 2H) 2.07-2.19 (m, 1H) 2.63-2.78 (m, 1H) 2.79-2.94 (m, 1H) 3.73 (s, 3H) 4.23-4.38 (m, 1H) 4.51-4.65 (m, 1H) 4.98-5.16 (m, 2H) 6.10-6.23 (m, 1H) 6.39-6.52 (m, 1H) 7.27-7.43 (m, 5H).

3-{[(Benzyloxy)carbonyl]amino}bicyclo[2.2.2]oct-5-ene-2-carboxylic acid

Methyl 3-{[(benzyloxy)carbonyl]amino}bicyclo[2.2.2]oct-5-ene-2-carboxylate (790 mg, 2.51 mmol) was dissolved in a mixture of THF/MeOH/H2O (1:1:1, 30 mL). Lithium hydroxide (525 mg, 12.51 mmol) was added and the mixture stirred at room temperature for 18 hours, followed by 2.5 hours at 50° C. The solvent was removed and the residue re-dissolved in water. The solution was extracted several times with chloroform and the organic layers discarded. The aqueous layer was then acidified to pH 1 with 6N HCl. The aqueous layer was then extracted several times with a mixture of THF/DCM (7:3). The organic layers were combined, washed with brine, and dried over sodium sulfate. The solvent was removed under reduced pressure and vacuum dried for two hours to give 3-{[(benzyloxy)carbonyl]amino}bicyclo[2.2.2]oct-5-ene-2-carboxylic acid as a sticky white foam which was used without further purification (710 mg, 94.0%). ¹H NMR (300 MHz, CHLOROFORM-d) d ppm 0.96-1.19 (m, 1H) 1.20-1.40 (m, 1H) 1.46-1.81 (m, 2H) 2.10-2.26 (m, 1H) 2.58-2.79 (m, 1H) 2.85-3.03 (m, 1H) 4.05-4.29 (m, 1H) 4.73-4.93 (m, 1H) 5.08 (d, J=5.65 Hz, 2H) 6.09-6.33 (m, 1H) 6.40-6.60 (m, 1H) 7.34 (s, 5H).

Benzyl (3-carbamoylbicyclo[2.2.2]oct-5-en-2-yl)carbamate

3-{[(Benzyloxy)carbonyl]amino}bicyclo[2.2.2]oct-5-ene-2-carboxylic acid (1.17 g, 3.88 mmol) was dissolved in acetonitrile (60 mL). A mixture of ammonium bicarbonate (460 mg, 5.82 mmol), BOC₂O (1.27 g, 5.82 mmol) and pyridine (154 mg, 1.95 mmol), in acetonitrile (20 was added and the combined mixture was stirred at room temperature for 18 hours. The solvent was removed under reduced pressure and the residue suspended in water. The suspension was sonicated for several minutes and then stirred for several minutes. The residue was removed by filtration, washed well with water, and vacuum dried to give benzyl (3-carbamoylbicyclo[2.2.2]oct-5-en-2-yl)carbamate as a white solid that was used without further purification (803 mg, 68.9%). NMR (300 MHz, CHLOROFORM-d) d ppm 0.94-1.16 (m, 1H) 1.19-1.40 (m, 1H) 1.71 (s, 2H) 1.96-2.17 (m, 1H) 2.54-2.76 (m, 1H) 2.94-3.19 (m, 1H) 3.90-4.14 (m, 1H) 4.78-4.98 (in, 1 II) 5.10 (s, 2H) 5.32-5.64 (m, 1H) 6.06-6.26 (m, 1H) 6.38-6.63 (m, 1H) 7.35 (s, 5H) 7.50-7.77 (m, 1H).

3-Aminobicyclo[2.2.2]octane-2-carboxamide

Benzyl (3-carbamoylbicyclo[2.2.2]oct-5-en-2-yl)carbamate (205 mg, 0.683 mmol) was placed in methanol (50 mL) and purged with nitrogen. Palladium on carbon (10%, 70 mg) and triethylamine (10 drops) were then added and the mixture shaken under hydrogen, at 45 psi, for 19 hours. The catalyst was removed by filtration and the filtrate evaporated under reduced pressure. The residue was purified by preparative thin layer chromatography (silica, 20×20 cm plate; 1000 microns, CMA 80) to give 3-aminobicyclo[2.2.2] octane-2-carboxamide a white solid (96 mg, 83.5%). NMR (300 MHz, METHANOL-d₄) d ppm 1.14-1.81 (m, 12H) 2.01 (d, J=6.59 Hz, 1H) 3.16-3.22 (m, 1H). ESI MS m/z: Calculated for C₉H₁₆N₂O 168.24, Found 169.3 (M+H)*.

3-[2-(2-Benzyl-4-phenylbutanamido)acetamido]bicyclo[2.2.2]octane-2-carboxamide (R06039-691)

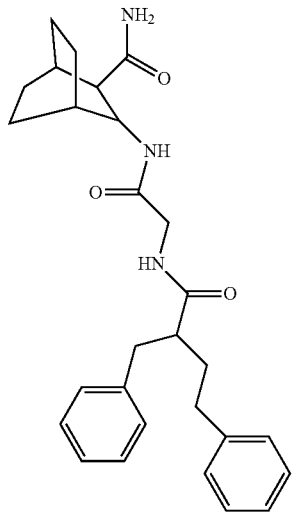 [SMILES: NC(=O)C1C2CCC(CC2)C1NC(=O)CNC(=O)C(CCc1ccccc1)Cc1ccccc1]

3-Aminobicyclo[2.2.2]octane-2-carboxamide (96 mg, 0.571 mmol), N-(2-benzyl-4-phenylbutanoyl)glycine (99 mg, 0.318 mmol) and triethylamine (257 mg, 2.54 mmol) were placed in dichloromethane (20 mL). EDC'HCl (109 mg, 0.569 mmol), and HOBt (77 mg, 0.570 mmol) were added and the mixture stirred at room temperature for 18 hours under nitrogen. At the end of this time, the solution was washed with saturated aqueous sodium chloride solution. The aqueous layer was then back extracted with dichloromethane, and the organic layers combined. The resulting solution was dried over sodium sulfate and the solvent was removed under reduced pressure. The residue was purified twice by preparative thin layer chromatography (silica, 20×20 cm plate, 1000 microns, 50% CMA 80/50% dichloromethane) to give R06039-691 as a white solid (44.0 mg; 30%). $^1$H NMR (300 MHz, CHLOROFORM-d) d ppm 1.28-1.92 (m, 10H) 1.95-2.25 (m, 3H) 2.37-3.03 (m, 5H) 3.55-3.94 (m, 2H) 4.07-4.32 (m, 1H) 5.39-5.65 (m, 1H) 6.45-6.73 (m, 1H) 6.94-7.43 (m, 12H). ESI MS m/z: Calculated for $C_{28}H_{35}N_3O_3$ 461.60, Found 462.6 (M+H)$^+$.

Synthesis of R06039-692

3-(Methoxycarbonyl)bicyclo[2.2.1]hept-5-ene-2-carboxylic acid

Bicyclo[2.2.1]heptane-2,3-dicarboxylic anhydride (1.0 g, 6.09 mmol) was dissolved in anhydrous tetrahydrofuran (3 mL) and cooled to 0° C. Sodium methoxide solution (0.5M, 18.27 mL, 9.14 mmol) was then added dropwise over 15 minutes. The solution was then allowed to warm to room temperature and stir for 2 hours. A second portion of sodium methoxide (9.14 mL, 4.57 mmol) was added and the mixture refluxed for 6.5 hours. The solution was allowed to cool to room temperature and stirred for an additional 14 hours. The reaction volume was reduced by approximately one half and the mixture poured into cold 2N HCl (50 mL). The resulting solution was extracted several times with chloroform, and the organic layers combined and dried over sodium sulfate. The solvent was removed under reduced pressure and the residue vacuum dried to give 3-(methoxycarbonyl)bicyclo [2.2.1]hept-5-ene-2-carboxylic acid as a white solid (926 mg, 77.5%). $^1$H NMR (300 MHz, CHLOROFORM-d) d ppm 1.48 (dd, J=8.76, 1.41 Hz, 1H) 1.63 (d, J=8.85 Hz, 1H) 2.66 (d, J=3.20 Hz, 1H) 3.14 (br. s., 1H) 3.30 (br. s., 1H) 3.43 (t, J=4.14 Hz, 1H) 3.67-3.84 (m, 3H) 6.14 (dd, J=5.46, 2.64 Hz, 1H) 6.29 (dd, J=5.37; 3.11 Hz, 1H).

Methyl 3-{[(benzyloxy)carbonyl]amino}bicyclo [2.2.1]hept-5-ene-2-carboxylate 3-(Methoxycarbonyl)bicyclo[2.2.1]hept-5-ene-2-carboxylic acid (880 mg, 4.49 mmol) was dissolved in toluene (15 mL). Diphenylphosphoryl azide (1.3 6 g, 4.94 mmol) and triethylamine (500 mg, 4.94 mmol) were added and the mixture heated at 90° C. for 2 hours. Benzyl alcohol (485 mg, 4.49 mmol) was then added and the mixture heated at 90° C. for 2 days, followed by stirring at room temperature for 18 hours. The mixture was diluted with ethyl acetate (100 mL) and extracted with saturated sodium bicarbonate solution several times. The organic layer was washed with brine, dried over sodium sulfate and the solvent removed under reduced pressure. The mixture was purified by silica gel chromatography (35% ethylacetate/55% hexane) to give methyl 3-[(benzyloxy)carbonyl]amino)bicyclo[2.2.1]hept-5-ene-2-carboxylate as a colorless liquid (930 mg, 68.8%). $^1$H NMR (300 MHz, CHLOROFORM-d) d ppm 1.42-1.57 (m, 1H) 1.77-1.86 (m, 1H) 1.92 (br. s., 1H) 2.87-3.14 (m, 2H) 3.73 (s, 3H) 4.41-4.65 (m, 2H) 5.08 (br. s., 2H) 6.09-6.24 (m, 1H) 6.33-6.49 (m, 1H) 7.27-7.43 (m, 5H).

3-{[(Benzyloxy)carbonyl]amino}bicyclo[2.2.1]hept-5-ene-2-carboxylic acid

Methyl 3-{[(benzyloxy)carbonyl]amino}bicyclo[2.2.1] hept-5-ene-2-carboxylate (910 mg, 3.02 mmol) was dissolved in a mixture of THF/MeOH/H$_2$O (1:1:1, 30 mL). Lithium hydroxide (600 mg, 14.3 mmol) was added and the mixture stirred at room temperature for 18 hours, followed by 2.5 hours at 50° C. The solvent was removed and the residue re-dissolved in water. The solution was extracted several times with chloroform and the organic layers discarded. The aqueous layer was then acidified to pH 1 with 6N HCl. The aqueous layer was then extracted several times with a mixture of THF/DCM (7:3). The organic layers were combined, washed with brine, and dried over sodium sulfate. The solvent was removed under reduced pressure and vacuum dried for 2.5 hours to give 3-{[(benzyloxy)carbonyl]amino}bicyclo[2.2.1]hept-5-ene-2-carboxylic acid as a white solid which was used without further purification (855 mg, 98.5%). NMR (300 MHz, CHLOROFORM-d) d ppm 1.55-1.70 (m, 1H), 1.75-1.90 (m, 1H), 2.05-2.15 (m, 1H), 3.03 (br. s., 1H) 3.90-4.00 (m, 1H) 4.12-4.32 (m, 1H) 4.73-5.01 (m, 1H) 5.05-5.20 (m, 2H) 6.01-6.28 (m, 1H) 6.44 (d, J=3.20 Hz, 1H) 7.18-7.45 (m, 5H).

Benzyl (3-carbamoylbicyclo[2.2.1]hept-5-en-2-yl) carbamate

3-{[(Benzyloxy)carbonyl]amino}bicyclo[2.2.1]hept-5-ene-2-carboxylic acid (850 mg, 2.96 mmol) was dissolved in acetonitrile (60 mL). A mixture of ammonium bicarbonate (351 mg, 4.44 mmol), BOC$_2$O (968 mg, 4.44 mmol) and pyridine (117 mg, 1.48 mmol), in acetonitrile (20 mL), was added and the combined mixture was stirred at room temperature for 17 hours. The solvent was removed under reduced pressure and the residue suspended in water. The suspension was sonicated for several minutes and then stirred for several minutes. The residue was removed by filtration, washed well with water, and vacuum dried to give benzyl (3-carbamoylbicyclo[2.2.1]hept-5-en-2-yl)carbamate as a white solid that was used without further purification (600 mg, 70.8%). $^1$H NMR (300 MHz, CHLOROFORM-d) d ppm 1.58 (s, 2H) 2.00 (br. s., 1H) 2.97 (br. s., 1H) 3.38 (br. s., 1H) 4.16-4.40 (m, 1H) 4.77 (d, J=6.78 Hz, 1H) 5.09 (q, J=12.06 Hz, 2H) 5.36-5.69 (m, 1H) 6.15 (dd, J=5.56, 2.54 Hz, 1H) 6.46 (dd, J=5.37, 3.11 Hz, 1H) 7.36 (s, 5H) 7.75-8.15 (m, 1H).

3-Aminobicyclo[2.2.1]heptane-2-carboxamide

Benzyl (3-carbamoylbicyclo[2.2.1]hept-5-en-2-yl)carbamate (225 mg, 0.786 mmol) was placed in methanol (75 mL) and purged with nitrogen. Palladium on carbon (10%, 100 mg) and triethylamine (10 drops) were added and the mixture shaken under hydrogen, at 45 psi, for 5 hours. The catalyst was removed by filtration and the filtrate evaporated under reduced pressure. The residue was purified by preparative thin layer chromatography (silica, 20×20 cm plate, 1000 microns, CMA 80) to give 3-aminobicyclo[2.2.1] heptane-2-carboxamide a white solid (95 mg, 78.5%). $^1$H NMR (300 MHz, METHANOL-d$_4$) d ppm 1.16-1.52 (m, 3H) 1.53-1.82 (m, 4H) 2.20 (br. s., 1H) 2.25-2.41 (m, 1H) 3.25-3.49 (m, 1H).

3-[2-(2-benzyl-4-phenylbutanamido)acetamido]bicyclo[2.2.1]heptane-2-carboxamide (R06039-692)

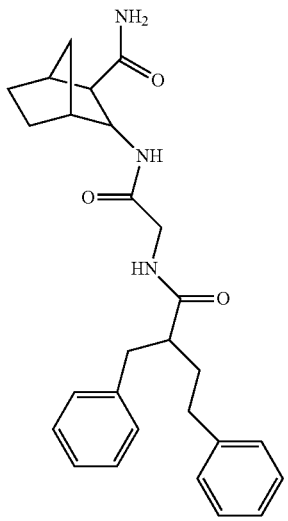 [SMILES: NC(=O)C1C2CCC(C2)C1NC(=O)CNC(=O)C(CCc1ccccc1)Cc1ccccc1]

3-Aminobicyclo[2.2.1]heptane-2-carboxamide (91 mg; 0.590 mmol), N-(2-benzyl-4-phenylbutanoyl)glycine (106 mg, 0.340 mmol) and triethylamine (276 mg, 2.73 mmol) were placed in dichloromethane (25 mL). EDCHCl (113 mg, 0.590 mmol), and HOBt (80 mg, 0.592 mmol) were added and the mixture stirred at room temperature for 18 hours under nitrogen. At the end of this time, the solution was extracted with saturated aqueous sodium chloride solution. The aqueous layer was back extracted with dichloromethane, and the organic layers combined. The solution was dried over sodium sulfate and the solvent removed under reduced pressure. The residue was purified twice by preparative thin layer chromatography (silica, 20×20 cm plate, 1000 microns, 50% CMA 80/50% dichloromethane) to give R06039-692 as a white solid (44.4 mg; 29.1%). $^1$H NMR (300 MHz, CHLOROFORM-d) d ppm 1.14-1.95 (m, 9H) 1.95-2.18 (m, 1H) 2.26-3.04 (m, 6H) 3.54-3.97 (m, 2H) 4.01-4.22 (m, 1H) 5.24-5.53 (m, 1H) 6.21-6.48 (m, 1H) 6.94-7.39 (m, 10H) 7.64-7.93 (m, 1H). ESI MS m/z: Calculated for $C_{27}H_{33}N_3O_3$ 447.57, Found 448.8 (M+H)$^+$.

Synthesis of R06039-693, 694, 695

$N^2$-[(Benzyloxy)carbonyl]-$N^6$-(tert-butoxycarbonyl)-N-(2-carbamoylcyclohexyl)-L-lysinamide (2S)-2-{[(Benzyloxy)carbonyl]amino}-6-[(tert-butoxycarbonyl)amino]hexanoic acid (321 mg, 0.844 mmol) and HATU (400 mg, 1.05 mmol) were dissolved in DMF (10 mL) and stirred for 10 minutes. 2-Aminocyclohexanecarboxamide (150 mg, 1.06 mmol) in DMF (2 mL) was then added and the mixture stirred for an additional 10 minutes, before adding DIEA (273 mg, 2.11 mmol). This solution was stirred overnight at room temperature. Saturated aqueous sodium chloride solution (50 mL) was added, and the mixture stirred for 30 minutes. The mixture was extracted with ethyl acetate several times and the organic layers combined. The precipitate that formed in the combined organic layer was filtered off and washed well with ethyl acetate. This solid was vacuum dried overnight to give $N^2$-[(benzyloxy)carbonyl]-$N^6$-(tert-butoxycarbonyl)-N-(2-carbamoylcyclohexyl)-L-lysinamide (280 mg, 65.7%). NMR (300 MHz, METHANOL-$d_4$) d ppm 1.17-2.00 (m, 24H) 2.28 (d, J=11.87 Hz, 1H) 2.92-3.16 (m, 2H) 4.00 (d, J=7.35 Hz, 2H) 5.09 (br. s., 2H) 6.47-6.70 (m, 1H) 7.20-7.47 (m, 5H). ESI MS m/z: Calculated for $C_{26}H_{40}N_4O_6$ 504.62, Found 505.5 (M+H)$^+$.

$N^6$-(tert-Butoxycarbonyl)-N-(2-carbamoylcyclohexyl)-L-lysinamide $N^2$-[(Benzyloxy)carbonyl]-$N^6$-(tert-butoxycarbonyl)-N-(2-carbamoylcyclohexyl)-L-lysinamide (270 mg, 0.535 mmol) was placed in methanol (100 mL) and purged with nitrogen. Palladium on carbon (10%, 100 mg) and triethylamine (10 drops) were added and the mixture shaken under hydrogen, at 45 psi, for 17 hours. The catalyst was removed by filtration and the filtrate evaporated under reduced pressure to give $N^6$-(tert-butoxycarbonyl)-N-(2-carbamoylcyclohexyl)-L-lysinamide as a white solid that was used without further purification (175 mg, 88.4%). $^1$H NMR (300 MHz, METHANOL-$d_4$) d ppm 1.18-1.67 (m, 24H) 1.78 (d, J=10.17 Hz, 3H) 1.94 (d, J=9.80 Hz, 2H) 2.30 (d, J=7.35 Hz, 1H) 2.93-3.20 (m, 3H) 3.81-4.13 (m, 1H).

2-[(2S)-6-amino-2-(2-benzyl-4-phenylbutanamido)hexanamido]cyclohexane-1-carboxamide (R06039-693, 694, 695)

2-Benzyl-4-phenylbutanoic acid (96 mg, 0.378 mmol) and HATU (180 mg, 0.474 mmol) were dissolved in DMF (5 mL) and stirred for 10 minutes. $N^6$-(tert-butoxycarbonyl)-N-(2-carbamoylcyclohexyl)-L-lysinamide (175 mg, 0.472 mmol) in DMF (5 mL) was added and the mixture stirred for 10 minutes. DIEA (122 mg, 0.944 mmol) was subsequently added and the mixture stirred overnight at room temperature. Saturated aqueous sodium chloride solution (25 mL) was added and the mixture stirred for 10 minutes. The resulting precipitate was removed by filtration, washed well with water and vacuum dried to give a yellow solid. The solid was then purified by preparative thin layer chromatography (silica, 20×20 cm plate, 1000 microns, 50% CMA 80/50% dichloromethane) to give $N^2$-(2-benzyl-4-phenylbutanoyl)-$N^6$-(tert-butoxycarbonyl)-N-(2-carbamoylcyclohexyl)-L-lysinamide as a white solid (55 mg; 24.0%). ESI MS m/z: Calculated for $C_{35}H_{50}N_4O_5$ 606.80, Found 629.9 (M+Na)$^+$. The above material (50 mg; 0.082 mmol) was dissolved in dichloromethane (5 mL). TFA was added (1.5 mL) and the mixture stirred at room temperature for 3 hours. The solvent was removed under reduced pressure and the residue chased several times with dichloromethane. This residue was dissolved in a small amount of dichloromethane and precipitated with hexane. The solid was filtered and vacuum dried to give the title compound as the TFA salt (40.5 mg, mixture of 4 isomers, 79.19%). R06039-693: NMR (300 MHz, METHANOL-$d_4$) d ppm 0.64-0.97 (m, 2H) 0.99-1.98 (m, 18H) 2.02-2.28 (m, 1H) 2.32-2.94 (m, 7H) 3.58-3.90 (m, 1H) 3.95-4.27 (m, 1H) 6.80-7.34 (m, 10H). ESI MS m/z: Calculated for $C_{30}H_{42}N_4O_3$ 506.68, Found 507.4 (M+H)$^+$.

The solid from above (20 mg) was further purified by preparative thin layer chromatography (silica, 20×20 cm plate, 1000 microns, CMA 80), to give two major fractions. Fraction 1 (less polar, 5 mg, mixture of two isomers), R06039-694: $^1$H NMR (300 MHz, METHANOL-$d_4$) d ppm 0.51-0.95 (m, 2H) 0.98-1.96 (m, 18H) 2.00-2.29 (m, 1H) 2.67 (s, 7H) 3.58-3.86 (m, 1H) 3.94-4.28 (m, 1H) 6.89-7.26 (m, 10H). ESI MS m/z: Calculated for $C_{30}H_{42}N_4O_3$ 506.68, Found 507.4 (M+H)$^+$. Fraction 2 (more polar, 7 mg, mixture of two isomers), R06039-695: $^1$H NMR (300 MHz, METHANOL-d$_4$) d ppm 0.61-0.97 (m, 2H) 0.98-1.93 (m, 18H) 1.99-2.25 (m, 1H) 2.67 (s, 7H) 3.63-3.93 (m, 1H) 3.94-4.23 (m, 1H) 6.89-7.25 (m, 10H). ESI MS m/z: Calculated for C$_{30}$H$_{42}$N$_4$O$_3$ 506.68, Found 507.4 (M+H)$^+$.

Synthesis of R06039-696, 697, 698

Benzyl-{(1S)-5-[(tert-butoxycarbonyl)amino]-1-[(3-carbamoylbicyclo[2.2.2]oct-2-yl)carbamoyl]pentyl}carbamate (2S)-2-{[(Benzyloxy)carbonyl]amino}-6-[(tert-butoxycarbonyl)amino]hexanoic acid (215 mg, 0.565 mmol) and HATU (269 mg, 0.707 mmol) were dissolved in DMF (10 mL) and stirred for 10 minutes. 3-Aminobicyclo[2.2.2]octane-2-carboxamide (119 mg, 0.707 mmol) in DMF (2 mL) was then added and the mixture stirred for an additional 10 minutes, before adding DIEA (132 mg, 1.41 mmol). This solution was stirred overnight at room temperature. Saturated aqueous sodium chloride solution (50 mL) was added and the mixture stirred for 10 minutes. The reaction mixture was then filtered to leave a sticky, light pink residue. This material was dissolved in dichloromethane and washed with saturated aqueous sodium chloride solution. The organic layer was dried over sodium sulfate and the solvent removed under reduced pressure. The residue was vacuum dried to give benzyl (1S)-5-[(tert-butoxycarbonyl) amino]-1-[(3-carbamoylbicyclo[2.2.2]oct-2-yl)carbamoyl]pentyl carbamate as a light pink foam which was used without further purification (240 mg, 80.0%). $^1$H NMR (300 MHz, CHLOROFORM-d) d ppm 1.09-1.92 (m, 24H) 1.93-2.40 (m, 2H) 2.97-3.21 (m, 2H) 3.99-4.33 (m, 2H) 4.71-4.94 (m, 1H) 5.07 (d, J=5.46 Hz, 2H) 5.61-5.82 (m, 1H) 5.85-6.10 (m, 1H) 7.00-7.54 (m, 7H). ESI MS m/z: Calculated for C$_{28}$H$_{42}$N$_4$O$_6$ 530.66, Found 531.6 (M+H)$^+$.

tert-Butyl {(5S)-5-amino-6-[(3-carbamoylbicyclo[2.2.2]oct-2-yl)amino]-6-oxohexyl}carbamate Benzyl {(1S)-5-[(tert-butoxycarbonyl)amino]-1-[(3-carbamoylbicyclo[2.2.2]oct-2-yl)carbamoyl]pentyl}carbamate (240 mg, 0.452 mmol) was placed in methanol (100 mL) and purged with nitrogen. Palladium on carbon (10%, 100 mg) and triethylamine (15 drops) were added and the mixture shaken under hydrogen, at 45 psi, for 5 hours. The catalyst was removed by filtration and the solvent removed from the filtrate under vacuum. The residue was taken up in a small amount of dichloromethane and precipitated with hexane. This mixture as a whole was then evaporated and vacuum dried to give tert-butyl {(5S)-5-amino-6-[(3-carbamoylbicyclo[2.2.2]oct-2-yl)amino]-6-oxohexyl}carbamate as a white solid (175 mg, 97.6%). $^1$H NMR (300 MHz, METHANOL-d$_4$) d ppm 1.25-1.84 (m, 26H) 1.85-2.03 (m, 1H) 2.31-2.48 (m, 1H) 3.04 (t, J=6.88 Hz, 2H) 3.48-3.66 (m, 1H) 4.32-4.52 (m, 1H). ESI MS m/z: Calculated for C$_{20}$H$_{36}$N$_4$O$_4$ 396.52, Found 397.6 (M+H)$^+$.

3-[(2S)-6-amino-2-(2-benzyl-4-phenylbutanamido)hexanamido]bicyclo[2.2.2]octane-2-carboxamide (R06039-696, 697, 698)

2-Benzyl-4-phenylbutanoic acid (90 mg, 0.354 mmol) and HATU (168 mg, 0.442 mmol) were dissolved in DMF (6 mL) and stirred for 15 minutes. tert-Butyl{(5S)-5-amino-6-[(3-carbamoylbicyclo[2.2.2]oct-2-yl)amino]-6-oxohexyl}carbamate (175 mg; 0.441 mmol) in DMF (4 mL) was added and the mixture stirred for 10 minutes. DIEA (114 mg, 0.88 mmol) was subsequently added and the mixture stirred overnight at room temperature. Saturated aqueous sodium chloride solution (25 mL) was added and the mixture stirred for 30 minutes. The resulting sticky precipitate was removed by filtration and washed well with water. This residue was dissolved in dichloromethane-THF (70/30, 30 mL), washed with saturated sodium bicarbonate solution, and dried over sodium sulfate. The solvent was removed under reduced pressure and the residue dissolved in a small amount of dichloromethane. Hexane was added and the resulting solid removed by filtration. The solid was then purified by preparative thin layer chromatography (silica, 20×20 cm plate, 1000 microns, 50% CMA 80/50% dichloromethane) to give tert-butyl{(5S)-5-[(2-benzyl-4-phenylbutanoyl)amino]-6-[(3-carbamoylbicyclo[2.2.2]oct-2-yl)amino]-6-oxohexyl}carbamate as a white solid (109 mg; 48.7%). ESI MS m/z: Calculated for C$_{37}$H$_{52}$N$_4$O$_5$ 632.83, Found 634.0 (M+H)$^+$. The above material (103 mg; 0.163 mmol) was dissolved in dichloromethane (6 mL). TFA (2 mL) was added and the mixture stirred at room temperature for 3.5 hours. The solvent was removed under reduced pressure and the residue chased several times with dichloromethane. This residue was dissolved in dichloromethane-THF (70/30, 30 mL), washed with saturated sodium bicarbonate solution, saturated aqueous sodium chloride solution, and dried over sodium sulfate. The solvent was removed under reduced pressure and the solid triturated with dichloromethane to give the title compound as white solid (35.1 mg, mixture of 4 isomers, 40.5%). R06039-696: $^1$H NMR (300 MHz, METHANOL-d$_4$) d ppm 0.83-1.13 (m, 1H) 1.25-2.05 (m, 18H) 2.30-2.47 (m, 1H) 2.80 (s, 8H) 4.14-4.43 (m, 2H) 7.04-7.36 (m, 10H). ESI MS m/z: Calculated for C$_{32}$H$_{44}$N$_4$O$_3$ 532.72, Found 533.3 (M+H)$^+$. The filtrate from the above trituration was evaporated and purified by preparative thin layer chromatography (silica, 20×20 cm plate, 1000 microns, CMA 80), to give two major fractions. Fraction 1. (less polar, 15.2 mg, mixture of two isomers, 17.5%), R06039-697: NMR (300 MHz, METHANOL-d$_4$) d ppm 0.80 (s, 2H) 1.07-1.72 (m, 18H) 1.74-1.94 (m, 2H) 2.13-2.30 (m, 1H) 2.32-2.90 (m, 7H) 4.01-4.32 (m, 2H) 6.82-7.27 (m, 10H). ESI MS m/z: Calculated for C$_{32}$H$_{44}$N$_4$O$_3$ 532.72, Found 533.1 (M+H)$^+$. Fraction 2 (more polar, 17.1 mg, mixture of two isomers, 19.7%), R06039-698: $^1$H NMR (300 MHz, METHANOL-d$_4$) d ppm 0.79 (d, J=7.16 Hz, 2H) 1.08-1.70 (m, 18H) 1.79 (br. s., 2H) 2.12-2.29 (m, 1H) 2.33-2.89 (m, 7H) 4.21 (d, J=6.97 Hz, 2H) 6.92-7.22 (m, 10H). ESI MS m/z: Calculated for C$_{32}$H$_{44}$N$_4$O$_3$ 532.72, Found 533.5 (M+H)+.

Synthesis of R06039-715

Methyl (6-oxo-6,11-dihydro-5H-dibenzo[b,e]azepin-5-yl)acetate 5,11-Dihydro-6H-dibenzo[b,e]azepin-6-one (300 mg, 1.43 mmol) was dissolved in DMF (10 mL) and cooled in a ice bath. Sodium hydride (60%, 75 mg, 1.88 mmol) was added and the mixture stirred at 0° C. for 10 minutes and then at room temperature for 30 minutes. The mixture was again cooled to 0° C. and methyl bromoacetate (548 mg, 3.58 mmol) added over several minutes. After stirring for 30 minutes at 0° C., the mixture was allowed to warm to room temperature and stir overnight. The mixture was the poured into ice water and extracted several times with dichloromethane. The organic layers were combined, dried over sodium sulfate and the solvent removed under reduced pressure. The residue was purified by silica gel chromatography (60% ethylacetate/40% hexane) to give methyl (6-oxo-6,11-dihydro-5H-dibenzo[b,e]azepin-5-yl)acetate as a colorless solid (401 mg, 99.5%). $^1$H NMR (300 MHz, CHLOROFORM-d) d ppm 3.44-3.67 (m, 1H) 3.81 (s, 3H) 4.31-4.54 (m, 1H) 4.60-4.91 (m, 2H) 7.01-7.46 (m, 7H) 7.80 (dd, J=7.63, 1.22 Hz, 1H). ESI MS in/z: Calculated for $C_{17}H_{16}NO_3$ 281.31, Found 282.3 (M+H)$^+$.

(6-Oxo-6,11-dihydro-5H-dibenzo[b,e]azepin-5-yl)acetic acid. Methyl (6-oxo-6,11-dihydro-5H-dibenzo[b,e]azepin-5-yl)acetate (391 mg, 1.39 mmol) was dissolved in a mixture of THF/MeOH/H2O (1:1:1, 24 mL). Lithium hydroxide (292 mg, 6.96 mmol) was added and the mixture stirred at room temperature for 2.5 hours. The solvent was removed and the residue re-dissolved in water. The solution was then acidified to pH 1 with 6N HCl. The mixture was then extracted several times with chloroform. The organic layers were combined, washed with brine, and dried over sodium sulfate. The solvent was removed under reduced pressure. The residue was taken up in a small amount of dichloromethane and precipitated with hexane. This mixture as a whole was then evaporated and vacuum dried to give (6-oxo-6,11-dihydro-5H-dibenzo[b,e]azepin-5-yl)acetic acid as a white solid (305 mg, 82.2%). $^1$H NMR (300 MHz, DMSO-d$_6$) d ppm 3.75 (d, J=13.00 Hz, 1H) 4.27 (d, J=12.81 Hz, 1H) 4.45-4.87 (m, 2H) 7.04-7.51 (m, 7H) 7.60 (d, J=7.35 Hz, 1H) 12.87 (br. s., 1H). ESI MS m/z: Calculated for $C_{16}H_{13}NO_3$ 267.28, Found 268.3 (M+H)$^+$.

2-[2-(2-{10-oxo-9-azatricyclo[9.4.0.0^{3,8}]penta-deca-1(11), 3(8),4,6,12,14-hexaen-9-yl}acetamido)acetamido]cyclohexane-1-carboxamide (R06039-715)

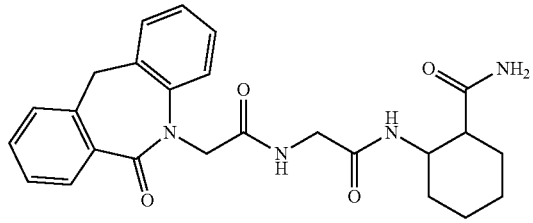 [SMILES: NC(=O)C1CCCCC1NC(=O)CNC(=O)CN1C(=O)c2ccccc2Cc2ccccc21]

(6-Oxo-6,11-dihydro-5H-dibenzo[b,e]azepin-5-yl)acetic acid (55 mg, 0.206 mmol) and HATU (98 mg, 0.258 mmol) were dissolved in DMF (3) and stirred for 10 minutes. DIEA (66 mg, 0.514 mmol) was then added and the mixture stirred for an additional 10 minutes, before adding 2-(glycylamino)cyclohexanecarboxamide (51 mg, 0.256 mmol) in DMF (3 mL). This solution was stirred overnight at room temperature. Saturated aqueous sodium chloride solution (25 mL) was added, and the mixture stirred for 30 minutes. The resulting precipitate was removed by filtration and washed well with water. This solid was triturated with a dichloromethane-methanol mixture and vacuum dried to give R06039-715 as an off-white solid (49.0 mg, 51.3%). Evaporation of the trituration filtrate provided a second crop of material (14.5 mg). $^1$H NMR (300 MHz, DMSO-d$_6$) d ppm 0.92-1.50 (m, 4H) 1.51-1.89 (m, 4H) 2.04-2.24 (m, 1H) 3.56-3.83 (m, 4H) 4.18-4.41 (m, 1H) 4.63 (br. s., 1H) 6.70 (br. s., 1H) 6.87-7.03 (m, 1H) 7.05-7.47 (m, 6H) 7.60 (d, J=7.16 Hz, 2H) 8.45 (br. s., 1H). ESI MS m/z: Calculated for $C_{25}H_{28}N_4O_4$ 448.51, Found 449.6 (M+H)$^+$.

Functional Determinations of EC50: Identification of functional agonists at the NPS receptor was done utilizing RD-HGA16 cells (Molecular Devices), a Chinese Hamster Ovary cell line stably expressing the promiscuous Gq-protein Gα16. RD-HGA16 cells were engineered to stably overexpress the NPS receptor. Two individual cell lines were created that stably express one of two human NPS receptor variants (NPS Ile107 and Asn107). Cells were loaded with a calcium sensitive dye (Molecular Devices) for 1 h at 370 C and compounds were assayed in separate experiments for intrinsic activity as measured by increased fluorescence intensity as a marker of mobilization of internal calcium stores using a FlexStation fluorescence plate reader. Compounds were run as 8-point full log or half log concentration curves in duplicate in order to determine the EC50 of the test compound. Each compound was tested in at least three independent experiments. A three-parameter logistic equation was fit to the concentration response data with Prism Software (v5 for Windows, GraphPad Software; San Diego, Calif.) to calculate the EC50 values. The data represent the mean±SEM from at least three independent experiments. Table 1 lists the EC50 for certain compounds of Formula I or Formula II.

TABLE 1

| Compound | EC50 (nM) |
|---|---|
| R06039-636 | 94 |
| R06039-641 | 169 |
| R06039-655 | 2107 |
| R06039-656 | 1020 |
| R06039-657 | 901 |
| R06039-675 | 213 |
| R06039-682 | 894 |
| R06039-691 | 93 |
| R06039-693 | 77 |
| R06039-696 | 91 |

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present disclosure, based on the description herein. Correspondingly, the subject matter as hereinafter claimed is intended to be broadly construed and interpreted, as including all such variations, modifications and alternative embodiments, within its spirit and scope.

What is claimed is:

1. A compound of Formula I:

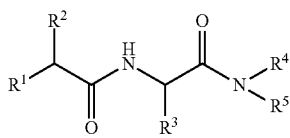

(I)

wherein:

$R^1$ is selected from phenyl, benzyl, benzyloxy, phenethyl, $C_1$-$C_4$ alkylcycloalkyl, benzamido, polycyclic heterocycle, or branched or unbranched $C_1$-$C_6$ alkyl;

$R^2$ is selected from benzyl;

$R^3$ is H, benzyl, or lysine side chain;

$R^4$ is
  (a) a five membered saturated ring substituted with one $C(O)NH_2$ group;
  (b) a six membered saturated or aromatic ring substituted with one $C(O)NH_2$ group,
  (c) $C_1$-$C_3$ amidoalkyl; and $R^5$ is H or $C_1$-$C_6$ alkyl;

or a pharmaceutically acceptable salt thereof.

2. The compound of claim 1, wherein:
$R^1$ is phenethyl;
$R^2$ is benzyl;
$R^4$ is a six membered saturated ring substituted with one $C(O)NH_2$ group, and
$R^3$ and $R^5$ are each H.

3. The compound of claim 1, wherein $R^1$ is phenyl or benzyl, and $R^2$ is benzyl.

4. The compound of claim 1, wherein $R^1$ is benzamido, $R^2$ is benzyl, $R^4$ is a six membered saturated ring substituted with one $C(O)NH_2$, and $R^5$ is methyl.

5. The compound of claim 1, wherein
$R^1$ is phenethyl, and
$R^4$ is a six membered saturated ring substituted with one $C(O)NH_2$.

6. The compound of claim 1, wherein
$R^1$ phenethyl, is
$R^2$ benzyl, is
$R^3$ is H or lysine side chain, and
$R^4$ is
  (a) a five membered saturated ring substituted with one $C(O)NH_2$ group, or
  (b) a six membered saturated or aromatic ring substituted with one $C(O)NH_2$ group.

7. A pharmaceutical composition comprising a compound according to claim 1 and a pharmaceutically acceptable carrier.

8. The compound of claim 1, wherein $R^1$ is benzamido, $R^2$ is benzyl, $R^4$ is $C_1$-$C_3$ amidoalkyl, and $R^5$ is H or benzyl.

9. The compound of claim 8, wherein $R^4$ is —CH($CH_2$)$CH_2C(O)NH_2$ or —CH(Ph)-CH—C(O)$NH_2$.

10. The compound of claim 1, wherein $R^1$ is $C_1$-$C_4$-alkylcycloalkyl, or branched or unbranched $C_1$-$C_6$-alkyl, $R^2$ is benzyl, $R^4$ is a six membered saturated ring substituted with one $C(O)NH_{21}$ and $R^3$ and $R^5$ are H.

11. The compound of claim 10, wherein $R^1$ is $CH_2CH_2$-cyclohexyl or isopentyl.

12. A method for treating a subject having a condition or disorder where modulation of neuropeptide S receptor activity is of therapeutic benefit, wherein such disorder or condition is selected from one or more of the group consisting of substance abuse, narcolepsy, insomnia, obesity, cognitive decline, dementia, Alzheimer's disease, panic disorder, generalized anxiety, PTSD, phobia, and schizophrenia, comprising administering to said subject in need thereof, a therapeutically effective amount of a compound according to claim 1.

13. The method of claim 12, further comprising administering an effective amount of a second active agent.

14. The compound selected from Formula II:

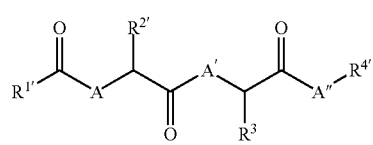

(II)

wherein $R^{1'}$ is phenyl;

$R^{2'}$ is benzyl;

A, A' and A" are independently selected from —NH— or —O—, provided that at least one of A, A' and A" is —O—;

$R^{3'}$ is H, benzyl or lysine side chain; and $R^{4'}$ is a five membered saturated ring substituted with one $C(O)NH_2$ group or a six membered saturated or aromatic ring substituted with one $C(O)NH_2$ group;

or a pharmaceutically acceptable salt thereof.

15. The compound of claim 14, wherein $R^{4'}$ is a six membered saturated ring substituted with one $C(O)NH_2$ group.

16. A pharmaceutical composition comprising a compound according to claim 14 and a pharmaceutically acceptable carrier.

17. A compound:

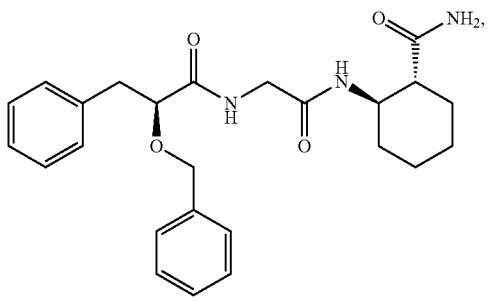 [SMILES: NC(=O)[C@@H]1CCCC[C@H]1NC(=O)CNC(=O)[C@H](Cc1ccccc1)OCc1ccccc1]

or a pharmaceutically acceptable salt thereof.

18. A pharmaceutical composition comprising a compound according to claim 17 and a pharmaceutically acceptable carrier.

19. A compound:

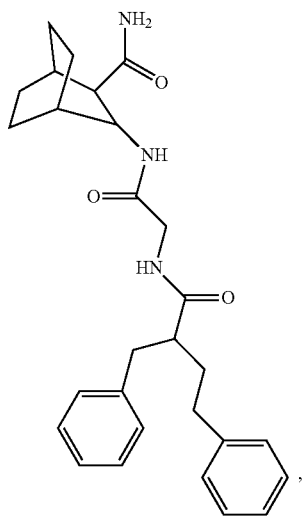 [SMILES: NC(=O)C1C2CCC(CC2)C1NC(=O)CNC(=O)C(CCc1ccccc1)Cc1ccccc1]

or a pharmaceutically acceptable salt thereof.

20. A pharmaceutical composition comprising a compound according to claim 19 and a pharmaceutically acceptable carrier.

21. A compound:

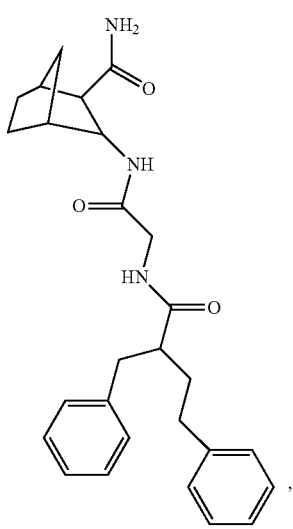 [SMILES: NC(=O)C1C2CCC(C2)C1NC(=O)CNC(=O)C(CCc1ccccc1)Cc1ccccc1]

or a pharmaceutically acceptable salt thereof.

22. A pharmaceutical composition comprising a compound according to claim 21 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 11,142,546 B2 | Page 1 of 1 |
| APPLICATION NO. | : 16/090726 | |
| DATED | : October 12, 2021 | |
| INVENTOR(S) | : Runyon et al. | |

It is certified that error appears in the above-identified patent and that said Letters Patent is hereby corrected as shown below:

In the Claims

In Claim 6
Column 47, Line 56, delete "R1 phenethyl, is" and insert therefore --R1 is phenethyl;--
Column 47, Line 57, delete "R2 benzyl, is" and insert therefore --R2 is benzyl;--
Column 47, Line 58, delete "chain," and insert --chain;--

In Claim 10
Column 48, Line 21, delete "$C(O)NH_{21}$" and insert therefore --$C(O)NH_2$,--

Signed and Sealed this
Sixth Day of September, 2022

*Katherine Kelly Vidal*

Katherine Kelly Vidal
*Director of the United States Patent and Trademark Office*

SEQUENCE LISTING

<160> NUMBER OF SEQ ID NOS: 1

<210> SEQ ID NO 1
<211> LENGTH: 20
<212> TYPE: PRT

```
<213> ORGANISM: Human

<400> SEQUENCE: 1

Ser Phe Arg Asn Gly Val Gly Thr Gly Met Lys Lys Thr Ser Phe Gln
1               5                   10                  15

Arg Ala Lys Ser
            20
```